(12) United States Patent
Miller

(10) Patent No.: US 10,758,251 B2
(45) Date of Patent: Sep. 1, 2020

(54) ADJUSTABLE DEVICE FOR IDENTIFYING A TARGET LOCATION FOR A TIBIAL TUNNEL AND RELATED METHOD THEREOF

(71) Applicant: University of Virginia Patent Foundation, Charlottesville, VA (US)

(72) Inventor: Mark D. Miller, Crozet, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 198 days.

(21) Appl. No.: 15/838,565

(22) Filed: Dec. 12, 2017

(65) Prior Publication Data

US 2018/0168665 A1  Jun. 21, 2018

Related U.S. Application Data

(60) Provisional application No. 62/437,092, filed on Dec. 21, 2016.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/17* | (2006.01) | |
| *A61B 17/32* | (2006.01) | |
| *A61B 17/04* | (2006.01) | |
| *A61B 17/00* | (2006.01) | |

(52) U.S. Cl.
CPC ...... *A61B 17/1714* (2013.01); *A61B 17/1764* (2013.01); *A61B 17/0401* (2013.01); *A61B 17/320016* (2013.01); *A61B 2017/00407* (2013.01)

(58) Field of Classification Search
CPC combination set(s) only.
See application file for complete search history.

(56) References Cited

U.S. PATENT DOCUMENTS

| | | | |
|---|---|---|---|
| 5,269,786 | A | 12/1993 | Morgan |
| 5,409,494 | A | 4/1995 | Morgan |
| 5,562,664 | A | 10/1996 | Durlacher |

(Continued)

FOREIGN PATENT DOCUMENTS

EP    2092900    8/2009

OTHER PUBLICATIONS

American Academy of Orthopaedic Surgeons (AAOS), "ACL Injury: Does it Require Surgery?", OrthoInfo, Sep. 2009, pp. 1-11, American Academy of Orthopaedic Surgeons.

(Continued)

*Primary Examiner* — Sameh R Boles
(74) *Attorney, Agent, or Firm* — Robert J. Decker

(57) ABSTRACT

An adjustable device for identifying the target location for, and placement of, a bone tunnel wherein the device is capable of measuring a total distance across a region of an anatomic structure. The device may be further configured to engage the anatomic structure at a target distance across the anatomic structure to identify the location for bone tunnel placement. A method for identifying the target location for, and placement of, a bone tunnel such that the method is capable of measuring a total distance across a region of an anatomic structure and capable of engaging the anatomic structure at a target distance across the anatomic structure.

29 Claims, 6 Drawing Sheets

(56) References Cited

U.S. PATENT DOCUMENTS

| | | | |
|---|---|---|---|
| 6,120,511 A * | 9/2000 | Chan | A61B 17/1637 606/102 |
| 6,254,605 B1 | 7/2001 | Howell | |
| 7,736,364 B2 | 6/2010 | Stone | |
| 8,298,239 B2 | 10/2012 | Re | |
| 8,444,652 B2 | 5/2013 | Amis | |
| 2012/0059382 A1 | 3/2012 | Paulos | |

OTHER PUBLICATIONS

Amis et al., "Anterior cruciate ligament graft positioning, tensioning and twisting", Knee Surgery, Sports Traumatology, Arthroscopy, 1998, pp. S2-S12, vol. 6, Suppl. 1.

Amis et al., "Functional Anatomy of the Anterior Cruciate Ligament: Fibre Bundle Actions Related to Ligament Replacements and Injuries", The Journal of Bone and Joint Surgery [Br], 1991, pp. 260-267, vol. 73-B.

Amis et al., "The functions of the fibre bundles of the anterior cruciate ligament in anterior drawer, rotational laxity and the pivot shift", Knee Surgery, Sports Traumatology, Arthroscopy, 2012, pp. 613-620, vol. 20, No. 4.

Astur et al., "Characterization of Cruciate Ligament Impingement: The Influence of Femoral or Tibial Tunnel Positioning at Different Degrees of Knee Flexion", Arthroscopy: The Journal of Arthroscopic and Related Surgery, 2013, pp. 913-919, vol. 29, No. 5.

Bedi et al., "Effect of Tibial Tunnel Position on Stability of the knee After Anterior Cruciate Ligament Reconstruction: Is the Tibial Tunnel Position Most Important?", The American Journal of Sports Medicine, 2011, pp. 366-373, vol. 39, No. 2.

Bovie Medical Corporation, "Cauteries", Accessed May 31, 2018, found at http://www.boviemedical.com/cauteries/.

Burnham et al., "Anatomic Femoral and Tibial Tunnel Placement During Anterior Cruciate Ligament Reconstruction: Anteromedial Portal All-Inside and Outside-In Techniques", Arthoscropy Techniques, 2017, e275-e282, vol. 6, No. 2.

Forsythe et al., "The Location of Femoral and Tibial Tunnels in Anatomic Double-Bundle Anterior Cruciate Ligament Reconstruction Analyzed by Three-Dimensional Computed Tomography Models", The Journal of Bone and Joint Surgery [AM], 2010, pp. 1418-1426, vol. 92.

Harner et al., "Anteromedial Portal Technique for Creating the Anterior Cruciate Ligament Femoral Tunnel", Arthroscopy: The Journal of Arthroscopic and Related Surgery, 2008, pp. 113-115, vol. 24, No. 1.

Hatayama et al., "The Importance of Tibial Tunnel Placement in Anatomic Double-Bundle Anterior Cruciate Ligament Reconstruction", Arthroscopy: The Journal of Arthroscopic and Related Surgery, 2013, pp. 1072-1078, vol. 29, No. 6.

Howell et al., "A rationale for predicting anterior cruciate graft impingement by the intercondylar roof. A magnetic resonance imaging study," Am J Sports Med, 1991, 19, pp. 276-282.

Howell et al., "Tibial Tunnel Placement in Anterior Cruciate Ligament Reconstructions and Graft Impingement", Clinical Orthopaedics and Related Research, 1992, pp. 187-195, No. 283.

Howell, "Arthroscopic Roofplasty: A Method for Correcting an Extension Deficit Caused by Roof Impingement of an Anterior Cruciate Ligament Graft", Arthroscopy: The Journal of Arthroscopic and Related Surgery, 1992, pp. 375-379, vol. 8, No. 3.

Hughes et al., "The use of intra-operative fluoroscopy for tibial tunnel placement in anterior cruciate ligament reconstruction", Bone & Joint Research, 2012, pp. 234-237, vol. 1, No. 10.

Irarrazaval et al., "Anterior cruciate ligament reconstruction", Journal of ISAKOS: Joint Disorders & Orthopaedic Sports Medicine, 2016, pp. 38-52, vol. 1.

Iriuchishima et al., "Evaluation of ACL mid-substance cross-sectional area for reconstructed autograft selection", Knee Surgery, Sports Traumatology, Arthroscopy, 2014 (published online 2012), pp. 207-213, vol. 22, No. 1.

Jackson et al., "Tibial Tunnel Placement in ACL Reconstruction", Arthroscopy, 1994, pp. 124-131, vol. 10, No. 2.

Kassam et al., "Anatomic Anterior Cruciate Ligament Reconstruction: The Use of the Anterior of the Lateral Meniscus as a Guide to Tibial Tunnel Placement", Arthroscopy Techniques, 2016, pp. e809-e814, vol. 5, No. 4.

Kasten et al., "What is the role of intra-operative fluoroscopic measurements to determine tibial tunnel placement in anatomical anterior cruciate ligament reconstruction?", Knee Surgery, Sports Traumatology, Arthroscopy, 2010, pp. 1169-1175, vol. 18, No. 9.

Kondo et al., "Biomechanical Analysis of knee Laxity With Isolated Anteromedial or Posterolateral Bundle-Deficient Anterior Cruciate Ligament", Arthroscopy: The Journal of Arthroscopic and Related Surgery, 2014, pp. 335-343, vol. 30, No. 3.

Larson et al., "Radiation exposure During Fluoroarthroscopically Assisted Anterior Cruciate Reconstruction", The American Journal of Sports Medicine, 1995, pp. 462-464, vol. 23, No. 4.

Lorenz et al., "Radiologic Evaluation of the Insertion Sites of the 2 Functional Bundles of the Anterior Cruciate Ligament Using 3-dimensional Computed Tomography", The American Journal of Sports Medicine, 2009, pp. 2368-2376, vol. 37, No. 12.

Matava et al., "Multirater Agreement of the Causes of Anterior Cruciate Ligament Reconstruction Failure: A Radiographic and Video Analysis of the MARS Cohort", The American Journal of Sports Medicine, 2014, pp. 310-319, vol. 43, No. 2.

Moloney et al., "Use of a Fluoroscopic Overlay to Assist Arthroscopic Anterior Cruciate Ligament Reconstruction", The American Journal of Sports Medicine, 2013, pp. 1794-1800, 41, No. 8.

Morgan et al., "Definitive Landmarks for Reproducible Tibial Tunnel Placement in Anterior Cruciate Ligament Reconstruction", Arthroscopy: The Journal of Arthroscopic and Related Surgery, 1995, pp. 275-288, vol. 11, No. 3.

Morgan et al., "Femoral Tunnel Malposition in ACL Revision Reconstruction", Journal of Knee Surgery, 2012, pp. 361-368, vol. 25, No. 5.

Pinczewski et al., "Radiological landmarks for placement of the tunnels in single-bundle reconstruction of the anterior cruciate ligament", The Journal of Bone and Joint Surgery [Br], 2008, pp. 172-179, vol. 90-B.

Seon et al., "In Vivo Stability and Clinical Comparison of Anterior Cruciate Ligament Reconstruction Using Low or High Femoral Tunnel Positions", The American Journal of Sports Medicine, 2011, pp. 127-133, vol. 39, No. 1.

Shimodaira et al., "Tibial Tunnel Positioning Technique Using Bony/Anatomical Landmarks in Anatomical Anterior Cruciate Ligament Reconstruction", Arthroscopy Techniques, 2017, pp. e49-e55, vol. 6, No. 1.

Smith & Nephew, "Acufex Director: Drill Guide", Web. Accessed May 31, 2018, 2 pages, http://www.smith-nephew.com/professional/products/all-products/acufex-director/.

Sommer et al., "Improperly placed anterior cruciate ligament grafts: correlation between radiological parameters and clinical results", Knee Surgery, Sports Traumatology, Arthroscopy, 2000, pp. 207-213, vol. 8, No. 4.

Staubli et al., "Tibial attachment area of the anterior cruciate ligament in the extended knee position. Anatomy and cryosections in vitro complemented by magnetic resonance arthrography in vivo", Knee Surgery, Sports Traumatology, Arthroscopy, 1994, pp. 138-146, No. 2.

Steiner et al., "Independent Drilling Outperforms Conventional Transtibial Drilling in Anterior Cruciate Ligament Reconstruction", The American Journal of Sports Medicine, 2009, pp. 1912-1919, vol. 37, No. 10.

Tompkins et al., "Anatomic Femoral Tunnel Drilling in Anterior Cruciate Ligament Reconstruction: Use of an Accessory Medial Portal Versus Traditional Transtibial Drilling", The American Journal of Sports Medicine, 2012, pp. 1313-1321, vol. 40, No. 6.

Werner et al., "A Prospective evaluation of the anterior horn of the lateral meniscus as a landmark for tibial tunnel placement in anterior cruciate ligament (ACL) reconstruction", The Knee, 2016, pp. 478-481, vol. 23, No. 3.

Wolf et al., "Variability in ACL Tunnel Placement: Observational Clinical Study of Surgeon ACl Tunnel Variability", The American Journal of Sports Medicine, 2013, pp. 1265-1273, 41, No. 6.

(56) References Cited

OTHER PUBLICATIONS

Zantop et al., "Tunnel Positioning of Anteromedial and Posterolateral Bundles in Anatomic Anterior Cruciate Ligament Reconstruction: Anatomic and Radiographic Findings", The American Journal of Sports Medicine, 2008, pp. 65-72, vol. 36, No. 1.

Ziegler et al., "Arthroscopically Pertinent Landmarks for Tunnel Positioning in Single-Bundle and Double-Bundle Anterior Cruciate Ligament Reconstructions", The American Journal of Sports Medicine, 2011, pp. 743-752, vol. 39, No. 4.

\* cited by examiner

ADJUSTABLE DEVICE FOR IDENTIFYING A TARGET LOCATION FOR A TIBIAL TUNNEL AND RELATED METHOD THEREOF

RELATED APPLICATIONS

The present application claims benefit of priority under 35 U.S.C. § 119 (e) from U.S. Provisional Application Ser. No. 62/437,092, filed Dec. 21, 2016, entitled "ACL Tibial Guide Device and Related Method Thereof," the disclosure of which is hereby incorporated by reference herein in its entirety.

FIELD OF INVENTION

The present invention has a broad application in the field of orthopedic surgery. Certain embodiments of the present invention may be utilized in any setting where a bone tunnel must be placed. More particularly, specific applications of certain embodiments of the present invention relate to the identification of a target location for, and placement of, a tibial bone tunnel during anterior cruciate ligament (ACL) reconstructive surgery.

BACKGROUND

Injuries to the anterior cruciate ligament (ACL) are a common occurrence. Though mild ACL injuries may be treated non-surgically, completely ruptured ACLs typically require surgical reconstruction. See generally American Academy of Orthopaedic Surgeons, *ACL Injury: Does it Require Surgery?*, OrthoInfo (September 2009), https://orthoinfo.aaos.org/en/treatment/acl-injury-does-it-require-surgery [AAOS, OrthoInfo (September 2009)]. Surgically repaired ACLs have a high rate of failure, and thus the damaged ACL is usually removed and replaced by a substitute graft during surgery. [AAOS, OrthoInfo (September 2009)] Current reconstructive techniques involve placing and securing a graft so as to recreate the biomechanical properties of the original ligament. See, e.g., Brian C. Werner et al., *A Prospective Evaluation of the Anterior Horn of the Lateral Meniscus as a Landmark for Tibial Tunnel Placement in Anterior Cruciate Ligament (ACL) Reconstruction*, 23 The Knee 478 (2016). During a typical reconstructive procedure, bone tunnels are drilled into the femur and tibia in order to receive and secure the graft. Sebastián Irarrázaval et al., *Anterior Cruciate Ligament Reconstruction*, 1 J. ISAKOS 38 (2016). Common graft options include hamstring tendon autographs, bone-patellar tendon-bone autografts, quadricep tendon autografts, and allografts. Irarrázaval et al. After the graft is pulled through the drilled bone tunnels, devices such as bone plugs, metal screws, or bio-interference screws are typically employed to securely fix the graft to the femur and tibia. Irarrázaval et al.

Improper positioning of the femoral or tibial tunnel are the most commonly cited reasons for graft failure. Werner et al. There is no consensus regarding the most effective position or orientation of the femoral tunnel. Werner et al. For example, vertically oriented femoral tunnels have been associated with an inability to control rotational forces across the surgically repaired knee. Werner et al. Studies suggest that horizontally oriented femoral tunnels placed independently of tibial tunnels may mitigate the drawbacks associated with vertically oriented femoral tunnels. Werner et al. However, there is currently no efficient manner in identifying the most effective position and orientation of the femoral tunnel. Werner et al.

The proper location of the tibial tunnel is also disputed. Werner et al. Variation in tibial tunnel placement can have detrimental effects on the success of the reconstructive procedure and the long-term prognosis for the surgically repaired knee. Werner et al. Studies suggest that placement of the tibial tunnel too posterior across the tibial plateau results in diminished knee stability. Conversely, a placement too anterior can result in graft impingement during knee extension. Werner et al. Historically, the recommended location for the tibial tunnel was in the center of the anatomic tibial footprint. Werner et al.

Certain techniques involve placing the tibial tunnel in reference to one or more intra-articular anatomic landmarks. For example, Kassam et al. describe a technique in which the tibial tunnel is placed in reference to the posterior border of the anterior horn of the lateral meniscus. Al-Amin M. Kassam et al., *Anatomic Anterior Cruciate Ligament Reconstruction: The Use of the Anterior of the Lateral Meniscus as a Guide to Tibial Tunnel Placement*, 5 Arthroscopy Techniques 809 (2016). Parsons' knob and the medial intercondylar ridge have also been described as bony landmarks to define a reference boundary to aid in positioning the tibial tunnel. Hiroki Shimodaira et al., *Tibial Tunnel Positioning Technique Using Bony/Anatomical Landmarks in Anatomical Anterior Cruciate Ligament Reconstruction*, 6 Arthroscopy Techniques 49 (2017). Additionally, the posterior cruciate ligament (PCL) is a commonly referenced anatomic landmark. For example, Burnham et al. recommend placing the tibial tunnel fifteen millimeters anterior to the PCL, in line with the posterior edge of the anterior horn of the lateral meniscus. Jeremy M. Burnham et al., *Anatomic Femoral and Tibial Tunnel Placement During Anterior Cruciate Ligament Reconstruction: Anteromedial Portal All-Inside and Outside-In Techniques*, 6 Arthroscopy Techniques 275 (2017). Zantop et al. and Morgan et al. likewise describe the proper tibial tunnel location in reference to an anterior displacement from the PCL. Thore Zantop et al., *Tunnel Positioning of Anteromedial and Posterolateral Bundles in Anatomic Anterior Cruciate Ligament Reconstruction*, 36 Am. J. Sports Med. 65 (2008); Craig D. Morgan et al., *Definitive Landmarks for Reproducible Tibial Tunnel Placement in Anterior Cruciate Ligament Reconstruction*, 11 J. Arthroscopic and Related Surgery 275 (1995). It should be appreciated that there is a lack of consensus in these approaches, particularly in terms of the magnitude of displacement from the referenced anatomic structures.

Other approaches seek to incidentally place the tibial tunnel in the center of the anatomic tibial footprint as defined by radiographic measurements. Werner et al. (citing H. U. Staubli & W. Rauschning, *Tibial Attachment Area of the Anterior Cruciate Ligament in the Extended Knee Position—Anatomy and Cryosections In Vitro Complemented by Magnetic Resonance Arthrography In Vivo*, 2 Knee Surgery, Sports Traumatology, Arthroscopy 138 (1994)). Many surgeons believed that placing the tibial tunnel in reference to intra-articular landmarks would result in a tibial tunnel location closely corresponding to the center of the anatomic tibial footprint as defined by radiographic measurements. Werner et al. However, recent research indicates that placing the tibial tunnel in reference to intra-articular landmarks, such as the lateral meniscus, results in inconsistent tibial tunnel locations and a variance of tibial tunnel locations relative to the center of the anatomic tibial footprint. Werner et al. In particular, placing the tibial tunnel in reference to the lateral meniscus has been demonstrated to result in an average tibial tunnel location anterior to the center of the anatomic tibial footprint. Werner et al. As discussed, among other drawbacks, this may increase the risk of graft impingement during knee extension. Werner et al.

The present inventor notes, as disclosed herein pertaining to embodiments of the present invention, that it is useful to place the tibial tunnel at a predefined percentage across the anterior-posterior distance of the tibial plateau. This approach will account for, among other things, differences in individual patient anatomy, improve technique reproducibility, and mitigate the risks herein discussed associated with tunnel malpositioning.

Some currently available devices, such as those disclosed in U.S. Pat. Nos. 5,269,786, 5,409,494, and 5,562,664 to Morgan et al., reference the PCL as an anatomic landmark and place the tibial tunnel at a fixed distance anterior to the leading edge of the PCL. Other devices, such as those disclosed by Howell in U.S. Pat. No. 6,254,605, mention landmarks to place the tibial tunnel in reference thereto. Similarly, other devices, such as those disclosed by Paulos in U.S. patent application Ser. No. 13/292,062 (U.S. Patent Application Publication No. US2012/0059382 A1), describe devices that may hook to a posterior region of a tibial plateau and provide apertures to drill a tibial tunnel at predetermined and fixed distances in reference thereto. Still others may allow a user to provide a tibial bone tunnel in reference to a first drilled femoral tunnel, as disclosed in U.S. Pat. No. 8,298,239 to Re, or at an offset from a first drilled bone tunnel, as disclosed in U.S. Pat. No. 7,736,364 to Stone. Other devices, such as the Acufex Director from Smith & Nephew are capable of placing a tibial tunnel on a tibial plateau (such as an anatomic landmark), but these devices lack the capability of measuring the tibial plateau and engaging the tibial plateau at a precise target distance. A description of the Acufex Director is available at http://www.smith-nephew.com/professional/products/all-products/acufex-director/. The aforementioned disclosures are herein incorporated by reference in their entirety.

No currently available device allows a user to measure the total distance across a tibial plateau and engage the tibial plateau at a precise target distance across the tibial plateau based upon a predetermined target percentage across the anterior-posterior distance of the tibial plateau. Moreover, no device provides this important advantage in a reproducible and consistent manner without the use of fluoroscopy or other imaging techniques.

SUMMARY OF EXEMPLARY EMBODIMENTS OF THE INVENTION

An embodiment of the present invention provides, but is not limited thereto, an adjustable device for locating a target location for bone tunnel placement in a subject. An aspect of an embodiment of the present invention device and related method provides, but is not limited thereto, measuring a total distance across a region of an anatomic structure and engaging the surface of the anatomic structure at a target distance across the region of the anatomic structure. This predetermined target distance may be calculated in reference to a predetermined percentage across the anterior-posterior distance of the region of the anatomic structure. Other embodiments of the present invention may also provide elements to place a guide pin (or other device or instrument) in reference to the identified target distance in order to drill and place a bone tunnel that exits at the target distance. Specific applications may include identifying a target distance across the anterior-posterior distance of a tibial plateau and optionally placing a guide pin in a tibia to assist in drilling a tibial bone tunnel during anterior cruciate ligament (ACL) reconstructive surgery.

In some non-limiting embodiments, the device may comprise a first arm, wherein the first arm may comprise an anterior portion and a posterior portion opposite said anterior portion.

The first arm may further comprise a plurality of graduated markings indicating units of length. Such markings may indicate, for example, units of length such as inches, centimeters, millimeters, or further divisions thereof. However, these are not required, and the first arm may have no markings, may have markings indicating a percentage across a region of an anatomic structure, or may have markings of any other suitable unit of length. Such markings may appear on the entire first arm or a portion of the first arm thereof.

In some non-limiting embodiments, the first arm may be substantially two-dimensional. However, this is not required, and in other suitable embodiments the first arm may have a three-dimensional shape. In those non-limiting embodiments, the first arm may have a cross-section of any suitable shape such as, for example, a circular, triangular, or rectangular cross-section. However, those skilled in the art will appreciate that the first arm can take on any variety of three-dimensional forms and shapes in order to meet situational or operational demands.

The posterior portion of the first arm may be configured to engage a reference structure, such as, for example, a posterior cruciate ligament or a posterior portion of a tibia. Accordingly, the posterior portion of the first arm may terminate in a point, curved hook, clasp, tip, claw, or suitable equivalents thereof.

The first arm may further comprise a targeting arm movably disposed on a surface of the first arm. The targeting arm may be disposed perpendicularly with respect to the first arm, but this is not required. That is, the targeting arm may protrude from the first arm at any alignment or angle to meet the operational or situational demands dictated by the use of the adjustable device. The targeting arm may be further configured to extend toward, engage with, and travel across a region of an anatomic structure, such as, for example, a tibial plateau.

In some non-limiting embodiments, the targeting arm may be substantially two-dimensional. However, this is not required, and in other suitable embodiments the targeting arm may have a three-dimensional shape. In those non-limiting embodiments, the targeting arm may have a cross-section of any suitable shape such as, for example, a circular, triangular, or rectangular cross-section. However, those skilled in the art will appreciate that the targeting arm can take on any variety of three-dimensional forms and shapes in order to meet the situational and operational demands.

The targeting arm may be further configured to engage across a region of an anatomic surface by terminating in a tapered point, hook, tip, or other suitable shape or form. However, this is not required, and in some non-limiting embodiments the shape of the targeting may be substantially uniform.

In some non-limiting embodiments, the targeting arm disposed on the first arm may be configured to move across the first arm. For example, and without limitation, the targeting arm may slide across the first arm, ratchet across the first arm, or rotate about a fixed point on the first arm. However, this is not required, and if the operational or situational demands dictate it, the targeting arm may remain statically disposed on the first arm in certain non-limiting embodiments. Moreover, the targeting arm may be further configured to vertically retract and extend from the first arm as it travels or advances across a region of the anatomic structure. That is, the targeting arm may be capable of maintaining constant contact with the surface of the anatomic structure as it moves across it by, for example, retracting into the first arm as it engages with and travels over an elevated portion of the anatomic surface or extending from the first arm as it engages with and travels over a depressed portion of the anatomic surface. This may be accomplished through a spring supplying an appropriate elastic force to the targeting arm. However, this is not required, and the targeting arm may maintain a constant vertical displacement from the first arm in other embodiments.

Further, in some non-limiting embodiments, the targeting arm may be further configured to withdraw so as to lay flush against the first arm or substantially parallel with the first arm (or other position so as to clear away from the anatomic surface). This may be accomplished by, for example, pivoting about a fixed point on the first arm.

In some non-limiting embodiments, the device may further comprise a targeting arm adjustment means that is configured to move the targeting arm. In other non-limiting embodiments, the targeting arm adjustment means may be further configured to withdraw the targeting arm such that the targeting arm lays flush against the first arm or substantially parallel with the first arm (or other position so as to clear away from the anatomic surface). The targeting arm adjustment means may be, but is not limited to, a dial, ratchet, switch, button, knob, or suitable equivalents thereof.

The targeting arm adjustment means may be electrically or manually operated. For example, the targeting arm adjustment means may control a motor or similar apparatus that is engaged with the targeting arm. This motor or similar apparatus may be powered using a battery, inductive power, or directly through a power cord. However, this is not required, and the targeting arm adjustment means may be directly coupled to the targeting arm such that the targeting arm is manually adjusted without electronic means.

The device may further comprise a second arm that is in communication with the anterior portion of the first arm. The second arm may further comprise a superior portion and an inferior portion opposite the superior portion.

In some non-limiting embodiments, the second arm may be substantially two-dimensional. However, this is not required, and in other suitable embodiments the second arm may have a three-dimensional shape. In those non-limiting embodiments, the second arm may have a cross-section of any suitable shape such as, for example, a circular, triangular, or rectangular cross-section. However, those skilled in the art will appreciate that the second arm can take on any variety of three-dimensional forms and shapes in order to meet situational and operational demands.

In some non-limiting embodiments, the second arm may be convexly curved. However, this is not required, and those skilled in the art will appreciate that the second arm may be substantially straight, slanted, or any other suitable shape or form in order to meet situational and operational demands.

The second arm may further comprise a measurement member. The measurement member may be configured to engage toward an anterior surface of a region of an anatomic structure such as, for example, a tibial plateau of a human being. Further, the measurement member may be aligned with the posterior portion of the first arm such that opposing ends of an anatomic region, such as, for example, a tibial plateau, may be simultaneously engaged by the measurement member and the posterior portion of the first arm.

In some non-limiting embodiments, the measurement member may further comprise a plurality of graduated markings indicating units of length. Such markings may indicate, for example, units of length such as inches, centimeters, millimeters, or further divisions thereof. However, these are not required, and the measurement member may have no markings, may have markings indicating a percentage across a region of an anatomic structure, or may have markings of any other suitable unit of length. Such markings may appear on the entire measurement member or a portion of the measurement member thereof.

In some non-limiting embodiments, the second arm may further comprise a slot that is configured to receive and accommodate the measurement member. However, this is not required, and the measurement member may alternatively be disposed, movably or otherwise, on a surface of the second arm. Further, the measurement member may be configured to move relative to the second arm by, for example and without limitation, sliding or ratcheting relative to the second arm. However, this is not required, and the measurement member may, in some non-limiting embodiments, be statically disposed on the second arm or statically disposed within a slot disposed on the second arm.

The second arm may also comprise a measurement member adjustment means that is configured to adjust the measurement member relative to the second arm. The measurement member adjustment means may be, for example and without limitation, a dial, ratchet, button, switch, plunger, rod or suitable equivalents thereof. The measurement member adjustment means may be disposed on the second arm and coupled with the measurement member or, in other embodiments, directly disposed on the measurement member.

Further, the measurement member adjustment means may be electrically or manually operated. For example, the measurement member adjustment means may control a motor or similar apparatus that is engaged with the measurement member. This motor or similar apparatus may be powered using a battery, inductive power, or directly through a power cord. However, this is not required, and the measurement member adjustment means may be directly coupled to the measurement member such that the measurement member is manually adjusted without electronic means.

In some non-limiting embodiments, the second arm may further comprise an outer portion and an inner portion disposed within the outer portion. The outer and inner portions of the second arm may be configured to move relative to each other in order to adjust the length of the second arm. However, this is not required, and the second arm may be of unitary construction and maintain a constant length.

In some non-limiting embodiments, the outer portion of the second arm may be disposed superiorly to the inner portion of the second arm. In other embodiments, the inner portion of the second arm may be disposed superiorly to the outer portion of the second arm. Further, the outer portion of the second arm may engage at least one surface of the inner portion of the second arm, and in other embodiments the outer portion of the second arm may completely envelop the inner portion of the second arm.

However, the outer portion of the second arm and inner portion are not required to directly engage one another, and in some non-limiting embodiments, the outer portion of the second arm and the inner portion may be offset. In these embodiments, the device may further comprise a means to separate the second arm. The means to separate the second arm may be, but is not limited to, a bracket, clamp, guide, bridge, claw, or similar equivalents thereof. The means to separate the second arm may engage a portion of one or both of the portions of the second arm on one or more of their respective surfaces, or the means to separate the second arm may completely envelop one or more portions of the second arm or completely envelop a smaller portion thereof. The means to separate the second arm may be further configured to allow the outer and inner portions of the second arm to move relative to one another. In some embodiments, the means to separate the second arm may remain in a fixed position, and in other embodiments the means to separate the second arm may move relative to one or both of the outer and inner portions of the second arm.

In some non-limiting embodiments, the second arm may further comprise a second arm adjustment means disposed on the second arm, wherein the second arm adjustment means is configured to adjust the length of the second arm by slidably moving the outer portion of the second arm and the inner portion of the second arm relative to each other. However, this is not required, and the second arm adjustment means may be configured to adjust the length of the second arm by moving the outer portion and inner portion of the second arm in any other suitable manner such as, for example, by ratcheting. The second arm adjustment means may be, but is not limited to, a button, knob, dial, ratchet, switch, or suitable equivalents thereof.

Further, the second arm adjustment means may be electrically or manually operated. For example, the second arm adjustment means may control a motor or similar apparatus that is engaged with one or more portions of the second arm. This motor or similar apparatus may be powered using a battery, inductive power, or directly through a power cord. However, this is not required, and the second arm adjustment means may be directly coupled to one or more portions of the second arm such that the length of the second arm is manually adjusted without electronic means.

In some non-limiting embodiments, the inferior portion of the second arm may be configured to engage and rest against a surface of an anatomic structure, such as, for example, a tibia of a human being. In these embodiments, the inferior portion of the second arm may terminate in a substantially flat and planar manner, or it may terminate in a manner that mimics the natural contour of an anatomic structure such as, for example, an anterior tibial surface. However, this is not required, and those skilled in the art will appreciate that the inferior portion of the second arm may terminate in a variety of suitable manners, forms, and shapes such that the inferior portion of the second arm may engage and rest against a surface of an anatomic structure. However, the second arm is not required to terminate in a manner such that it rests against a surface of an anatomic structure. For example, in other non-limiting embodiments, the second arm may terminate in a handle that allows the user to grasp and control the device during operation. Though, this is also not required.

In other non-limiting embodiments, the second arm may further comprise a guiding device disposed on the inferior portion of the second arm. The guiding device may be configured to receive and place a guide pin.

In certain non-limiting embodiments, the guide pin may be 3/32 of an inch. However, this is not required, and those of ordinary skill in the art will appreciate that a variety of guide pin sizes and gauges may be used as dictated by operational and structural demands.

Further, in some non-limiting embodiments, the guiding device may be adjustable. For example, the guiding device may pivot about a fixed point on an inferior portion of the second arm. In other embodiments, the guiding device may slide along a portion of the second arm, or ratchet across the second arm.

The guiding device may further comprise a guiding device adjustment means that is configured to adjust the orientation of the guiding device. For example, the guiding device adjustment means may adjust the angle of the guiding device with respect to the second arm. The guiding device adjustment means may be, but is not limited to, a knob, dial, button, switch, ratchet, nut, bolt, hinge, ball and socket joint, or other suitable equivalents thereof.

Further, the guiding device adjustment means may be electrically or manually operated. For example, the guiding device adjustment means may control a motor or similar apparatus that is engaged with the guiding device. This motor or similar apparatus may be powered using a battery, inductive power, or directly through a power cord. However, this is not required, and the guiding device adjustment means may be directly coupled to the guiding device such that the orientation of the guiding device is manually adjusted without electronic means.

In some non-limiting embodiments, identifying a target location for a bone tunnel in a subject is disclosed. This method may comprise 1) utilizing an adjustable device to engage a reference structure of the subject; 2) utilizing a measurement member of the adjustable device to measure a total distance across a region of an anatomic structure of the subject; 3) calculating a target distance across the region of the anatomic structure based upon a predetermined target percentage across the total distance, and; 4) engaging the anatomic structure at the target distance across the region of the anatomic structure by adjusting a targeting arm that is movably disposed on a first arm of the adjustable device. The adjustable device may be the adjustable device as herein described.

In some non-limiting embodiments, the method for identifying a target location for a bone tunnel may further comprise marking the identified target location at the target distance across the region of the anatomic structure. For example, and without limitation, a Bovie electrocautery device (or other type of electrocautery or marking device) may be utilized to mark the location of the anatomic structure engaged by the targeting arm at the target distance. A description of Bovie electrocautery devices is available at http://www.boviemedical.com/cauteries and is herein incorporated by reference in its entirety. However, in other embodiments, the identified target location may be marked using other techniques or devices. For example, a surgical pen or microfracture awl may also or alternatively be used to mark the identified target location for the bone tunnel.

The reference structure in some non-limiting embodiments may be the posterior end of the tibial plateau in a human being. In other embodiments, the reference structure may be a posterior cruciate ligament, or a region of the tibia laterally or anteriorly displaced from the attachment location of the posterior cruciate ligament.

The region of the anatomic structure in some non-limiting embodiments may be a tibial plateau of a human being. Accordingly, in these embodiments, the bone tunnel may be a tibial tunnel.

In some non-limiting embodiments, the predetermined target percentage across the region of the anatomic structure may be 35% of the anterior-posterior distance. However, this is not required, and the predetermined target percentage may be manipulated as dictated by the operational or situational demands, a patient's individual anatomy or medical requirements, or any other variable. It should be understood that 35% is meant to be exemplary rather than limiting or necessary. For example, the predetermined target percentage may include all numbers and fractions subsumed within the range of 0% through 100%.

In these embodiments, "0%" would refer to the extreme anterior end of the region of the anatomic structure. For example, "0%" may refer to the extreme anterior end of the tibial plateau. Thus, in these embodiments, "100%" would refer to the extreme posterior end of the region of the anatomic structure. For example, "100%" may refer to the extreme posterior end of the tibial plateau. However, these designations are meant to be exemplary rather than limiting or necessary. For example, these conventions may be reversed such that "0%" refers to the posterior end and "100%" refers to the anterior end.

In some non-limiting embodiments, the method for identifying a target location for a bone tunnel may further comprise adjusting a second arm of the adjustable device in accordance with the position of the targeting arm. This may be accomplished by, for example, calibrating the desired length of the second arm with respect to the position or displacement of the targeting arm. This calibration may be implemented such that a guiding device (or other instrument, device, or tool) disposed on an inferior portion of the second arm is aligned with the position of the targeting arm and such that the guiding device (or other instrument, device, or tool) engages a surface of an anatomic structure. The anatomic structure may be a tibia. It should be appreciated that proper calibration of the length of the second arm would be within the capability of those of ordinary skill in the art.

Arthroscopic techniques may be employed to calibrate the length of the second arm in accordance with the position of the targeting arm. However, this is not required, and those of ordinary skill in the art would appreciate that the required magnitude of adjustment of the length of the second arm could be calculated using available computational and adjustment techniques.

In other non-limiting embodiments, the method for identifying a target location for a bone tunnel may further comprise adjusting a guiding device (or other instrument, device, or tool) that may be disposed on an inferior portion of the second arm in accordance with the position or displacement of the targeting arm. This may be accomplished by, for example, calibrating the proper angle of the guiding device (or other instrument, device, or tool) in relation to the second arm based upon the location or displacement of the targeting arm. This calibration may be implemented such that the guiding device (or other instrument, device, or tool) is aligned with the position of the targeting arm as the guiding device (or other instrument, device, or tool) is engaged with a surface an anatomic structure. The anatomic structure may be a tibia. It should be appreciated that the proper calibration of the angle of the guiding device (or other instrument, device, or tool) could be accomplished using available computational and adjustment techniques or routine experimentation.

Arthroscopic techniques may be employed to calibrate the angle of the guiding device (or other instrument, device, or tool) with respect to the second arm in accordance with the position of the targeting arm. However, this is not required.

In other non-limiting embodiments, the method for identifying a target location for a bone tunnel may further comprise disengaging the adjustable device from the anatomic structure.

In some embodiments, the method for identifying a target location for a bone tunnel as disclosed herein may also further comprise utilizing currently available tibial tunnel guide devices to engage the region of the anatomic structure at the target distance. For example, the Acufex Director guide from Smith & Nephew may be utilized to engage the tibial plateau at the target distance identified by an embodiment of the present invention. However, the Acufex Director device is not required, and those of ordinary skill in the art will appreciate that a variety of suitable tools, devices, apparatuses, and implements may be utilized to place the tibial tunnel once the target distance is located. Further, the method may further comprise inserting a guide pin (or other instrument, device, or tool) into the anatomic structure at the location engaged by a tibial tunnel guide device (or other instrument, device, or tool) and drilling a tibial tunnel to the target location using a cannulated drill, reamer, or other suitable instrument, device, tool, or surgical technique.

It should be appreciated that the adjustable device herein disclosed is capable of measuring a total distance across an anatomic structure without the use of fluoroscopy or other imaging techniques. Further, embodiments of the disclosed device have the capability of engaging the anatomic structure at a precise distance across a region of the anatomic structure. Therefore, the present invention can be utilized to identify a target location for a bone tunnel at a target distance or target percentage across a region of an anatomic structure, such as, for example, a tibial plateau. Additionally, this device provides the important advantage of identifying this location based on the true distance across the tibial plateau, rather than based on an arbitrary displacement from an anatomic landmark. Moreover, this device allows for precise identification of a target location for a bone tunnel, rather than relying on estimation. These features will mitigate the risks associated with improper placement of the tibial tunnel, such as graft failure, reduction of knee mobility, and graft impingement.

It should be appreciated that the device and related components of the device discussed herein may take on all shapes along the entire continual geometric spectrum of manipulation of x, y, and z planes to provide and meet the anatomical, environmental, and structural demands, and operational requirements. Moreover, locations and alignments of the various components may vary as desired or required.

It should be appreciated that while some dimensions are provided on the aforementioned figures, the device may constitute various sizes, dimensions, contours, rigidity, shapes, flexibility, and materials as it pertains to the components or portions of components of the device, and therefore may be varied and utilized as desired or required.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an," and "the" include plural referents unless the context clearly dictates otherwise. Ranges may be expressed herein as from "about"

or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, or method steps, even if the other such compounds, material, particles, or method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, 4.24, and 5). Similarly, numerical ranges recited herein by endpoints include subranges subsumed within that range (e.g., 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

It should be appreciated that various sizes, dimensions, contours, rigidity, shapes, flexibility and materials of any of the components or portions of components in the various embodiments discussed throughout may be varied and utilized as desired or required.

The invention itself, together with further objects and attendant advantages, will best be understood by reference to the following detailed description, taken in conjunction with the accompanying drawings.

BRIEF DESCRIPTION OF THE DRAWINGS

The foregoing and other objects, features, and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF THE INVENTION

Turning now to the drawings, the subject invention, as shown in FIGS. 1-8 includes an adjustable device 11 for identifying a target location for a bone tunnel 45 in an anatomic structure such as, for example, a tibia 51.

An aspect of an embodiment of the present invention has a broad application in the field of orthopedic surgery. Exemplary applications of the technology herein disclosed include measuring a total distance across a region of an anatomic structure and identifying a target location for a bone tunnel based upon a predetermined target percentage across the anterior-posterior distance of the anatomic structure. Further applications of the technology herein disclosed may include placing a guide pin in accordance with the identified target location for a bone tunnel and drilling a bone tunnel. Additional non-limiting examples include measuring a total distance across a tibial plateau, engaging a region of the tibial plateau at a target distance, and drilling a tibial bone tunnel in accordance with the identified target distance across the tibial plateau during ACL reconstructive surgery.

Figure 1:
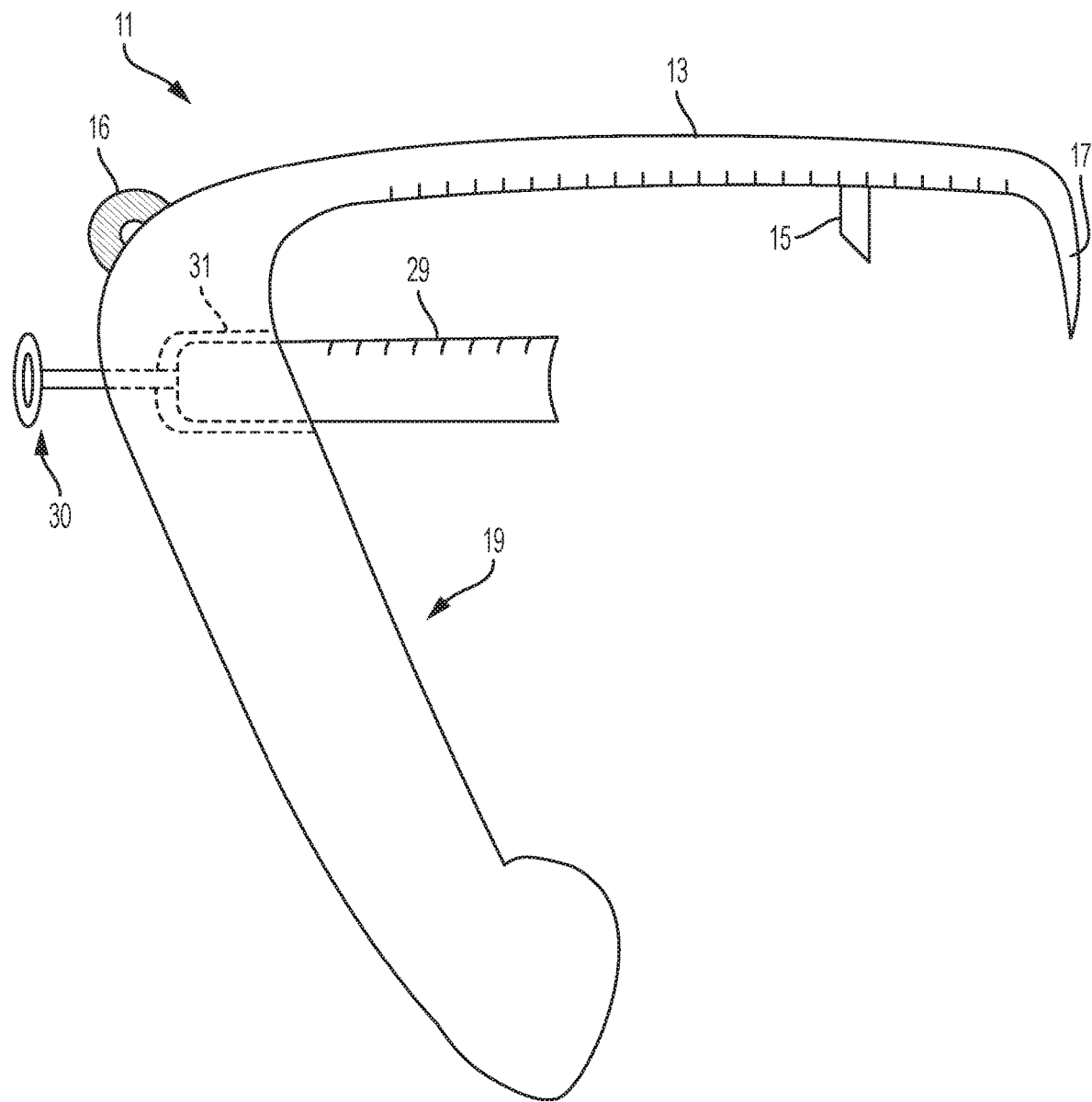
FIG. 1 is a schematic side view of a device in accordance with an embodiment.

FIG. 1 illustrates an exemplary and non-limiting embodiment of the present invention. An adjustable device 11 comprises a first arm 13 and a second arm 19 in communication with the first arm 13.

The first arm 13 further comprises a targeting arm 15 perpendicularly disposed on a surface of the first arm 13; or the targeting arm 15 may protrude from the first arm 13 at any alignment or angle to meet the operational or situational demands dictated by the use of the adjustable device 11. The first arm 13 further comprises a plurality of graduated markings indicating units of length. These units of length may be inches, centimeters, millimeters, or further divisions thereof. These markings may also or alternatively indicate graduated percentages across an anatomic structure.

The targeting arm 15 may be movably disposed on the first arm 13. For example, and without limitation, the targeting arm 15 may be configured to slide or ratchet across a surface of the first arm 13, or it may pivot about a fixed point on a surface of the first arm 13. The adjustable device 11 may further comprise a targeting arm adjustment means 16 disposed on a surface of the adjustable device 11. The targeting arm adjustment means 16 may be configured to adjust the location and orientation of the targeting arm 15.

Those skilled in the art will appreciate that the targeting arm adjustment means 16 may be in any form suitable to couple with, and adjust the location and orientation of, the targeting arm 15. For example, and without limitation, the targeting arm adjustment means 16 may be a dial, ratchet, button, switch, or suitable equivalents thereof. The targeting arm adjustment means 16 may be manually or electrically operated. For example, the targeting arm adjustment means 16 may be coupled to a motor or similar apparatus that is coupled to the targeting arm 15. This motor or similar apparatus may be powered using a battery, inductive power, or directly through a power cord. However, this is not required, and the targeting arm adjustment means 16 may be directly coupled to the targeting arm 15 such that the location and orientation of the targeting arm 15 may be manually adjusted without the use of electronic means.

In FIG. 1, the targeting arm 15 is depicted as a rectangular member that tapers and terminates in a point. However, this is not required, and the targeting arm 15 may take on a variety of forms and shapes. For example, and without limitation, the targeting arm 15 may be substantially two-dimensional or it may be three-dimensional with a circular, square, rectangular, or other suitably shaped cross-section. The targeting arm 15 may terminate in a tapered point, may retain a uniform shape throughout, or take on a variety of other shapes and forms as operational or situational demands dictate.

Figure 4:
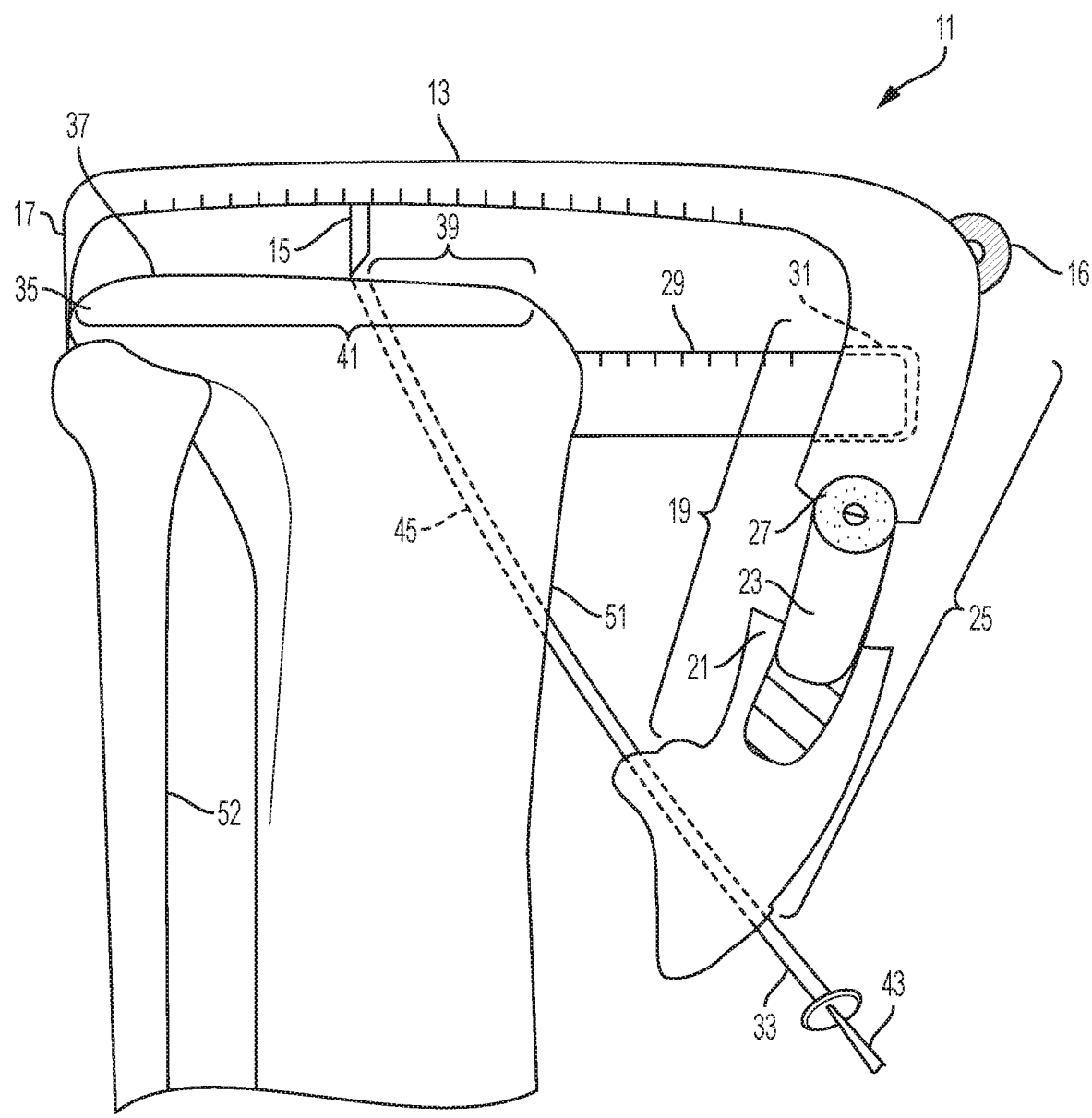
FIG. 4 is a schematic side view of an adjustable device in operation with associated anatomy in accordance with an embodiment.
Figure 5:
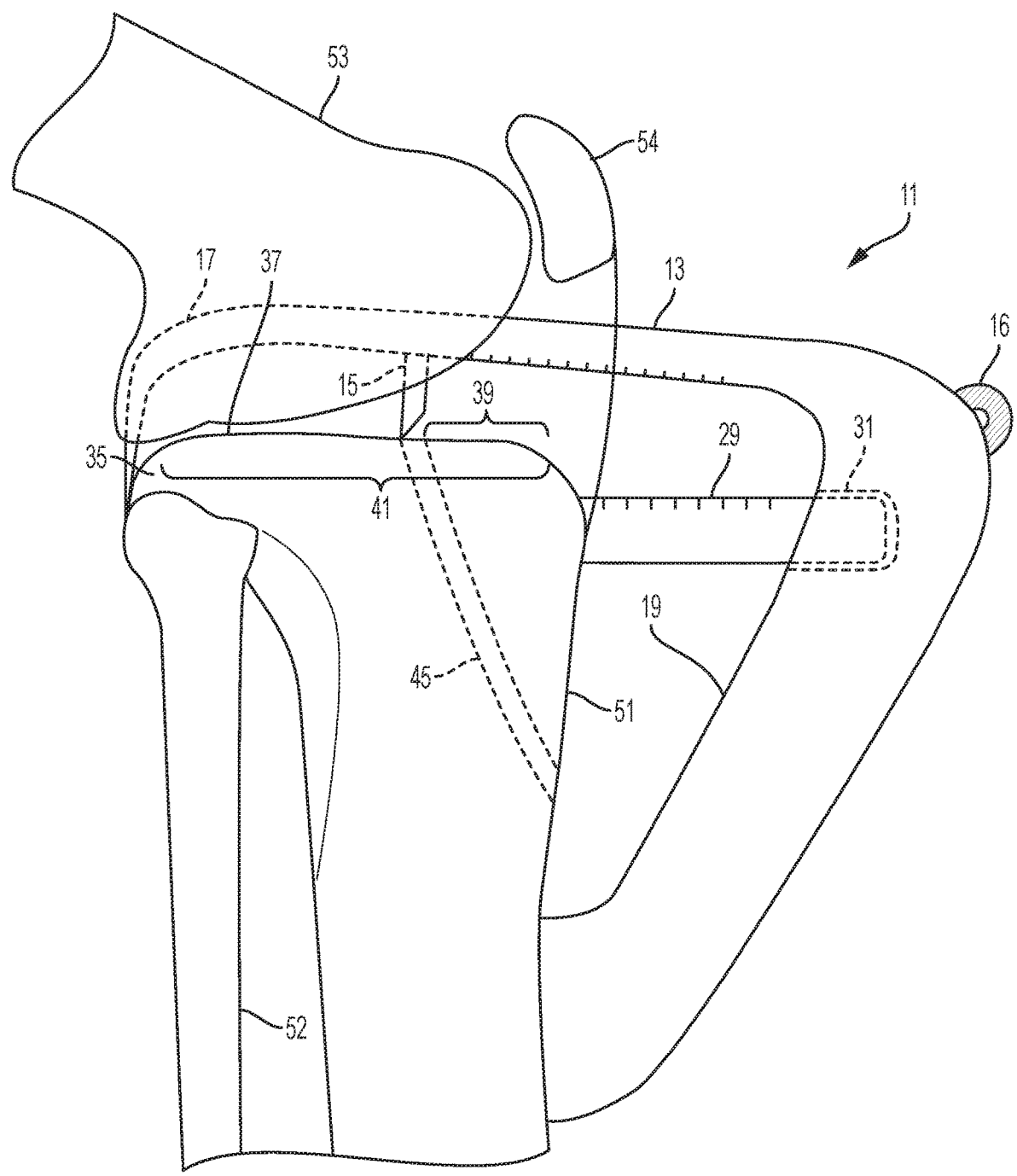
FIG. 5 is a schematic side view of an adjustable device in operation with associated anatomy in accordance with an embodiment.

In FIG. 1, the posterior region of the first arm 15 terminates in a curved hook 17. However, this is meant to be exemplary and not limiting, and the posterior region of the targeting arm 15 may terminate in any form suitable to engage a reference structure 35, as depicted in FIGS. 4 and 5. For example, the posterior region of the first arm 15 may alternatively terminate in a point, clasp, tip, claw, or suitable equivalents thereof.

Though not depicted in FIG. 1, the targeting arm 15 may be configured to withdraw so as to lay flush against the first arm 13 or substantially parallel with the first arm 13. This may be accomplished by, for example, rotating the targeting arm 15 about a fixed point on the first arm 13. Similarly, the targeting arm adjustment means 16 may be configured to perform such a withdrawal, or any other withdrawal such that the targeting arm 15 lays flush against the first arm 13, or substantially parallel with the first arm 13.

The curved hook 17 terminates in a point that is aligned with a measurement member 29 that is disposed on the second arm 19 such that the curved hook 17 and measurement member 29 can simultaneously engage opposing ends of a region of an anatomic structure. For example, FIGS. 4 and 5 depict the curved hook 17 and measurement member 29 simultaneously engaging opposite ends of a tibial plateau.

The measurement member 29 further comprises a plurality of graduated markings indicating units of length. These units of length may be inches, centimeters, millimeters, or further divisions thereof. These markings may also or alternatively indicate graduated percentages across an anatomic structure.

The measurement member 29 is accommodated within a slot 31 disposed on the second arm 19. The measurement member 29 is further configured to move within the slot 31 such that the measurement member 29 may move relative to the second arm 19. However, this is not required, and the measurement member 29 may alternatively be movably or statically disposed on a surface of the second arm 19, or the measurement member 29 may be statically disposed within the slot 31. Further, the measurement member 29 may be configured to move relative to the second arm 19 in any suitable manner such as, for example, by sliding or ratcheting. The slot 31 may be disposed within the second arm 19 or on an outer surface of the second arm 19.

FIG. 1 further depicts a measurement member adjustment means 30 protruding from a surface of the second arm 19 and coupled with the measurement member 29. The measurement member adjustment means 30 is depicted as a rod coupled with the measurement member 29 that terminates in a small knob. However, it should be appreciated that the measurement member adjustment means 29 may take on a variety of other forms, such as, but not limited to, a dial, ratchet, button, switch, plunger or suitable equivalents thereof.

As depicted in FIG. 1, the user may control the lateral displacement of the measurement member 29 within the slot 31 by pulling or pushing on the measurement member adjustment means 30. In an exemplary use of the present invention, a user would adjust the measurement member adjustment means 30 until the measurement member 29 lays flush against an anterior portion or edge of an anatomic surface, such as a tibial plateau, as illustrated in FIGS. 4 and 5.

In FIG. 1, the second arm 19 is in communication with the anterior region of the first arm 13. The second arm 19 is depicted as being convexly curved in FIG.1. However, this is not required, and the second arm 19 may be substantially straight, slanted, or otherwise shaped if operational or situational demands should dictate it to be.

FIG. 1 depicts the inferior portion of the second arm 19 terminating in a manner such that it may engage and rest against a surface of an anatomic surface. For example, in FIG. 5, the inferior portion of the second arm 19 rests against an anterior surface of a tibia 51. However, this is not required, and in other non-limiting exemplary embodiments the inferior portion of the second arm 19 may terminate such that it is not configured to rest against a surface of an anatomic structure. For example, the second arm 19 may alternatively terminate in a handle such that a user may grasp and control the adjustable device 11 during operation.

Figure 2:
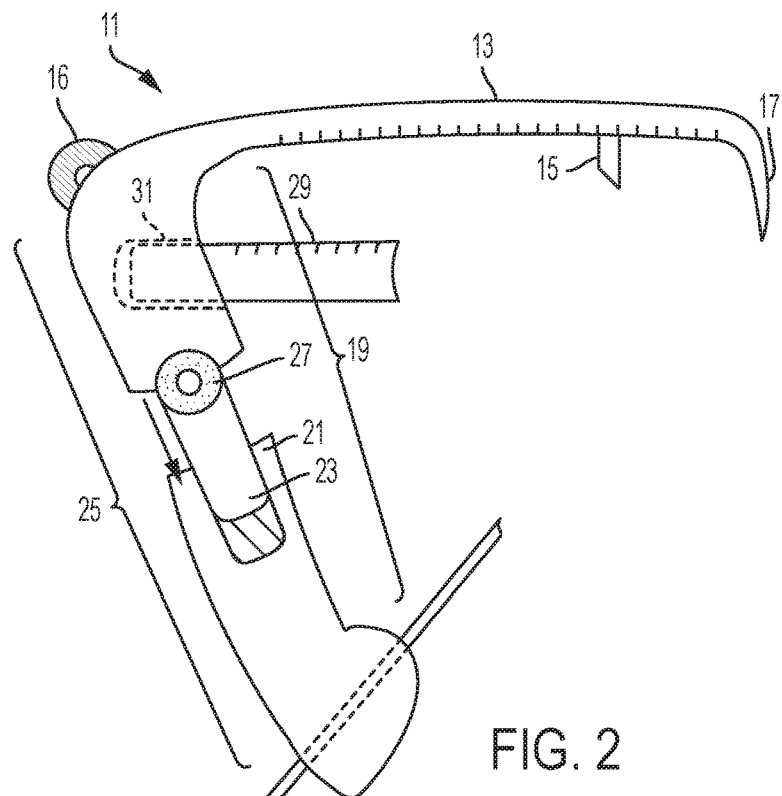
FIG. 2 is a schematic side view of an adjustable device in a protracted configuration in accordance with an embodiment.
Figure 3:
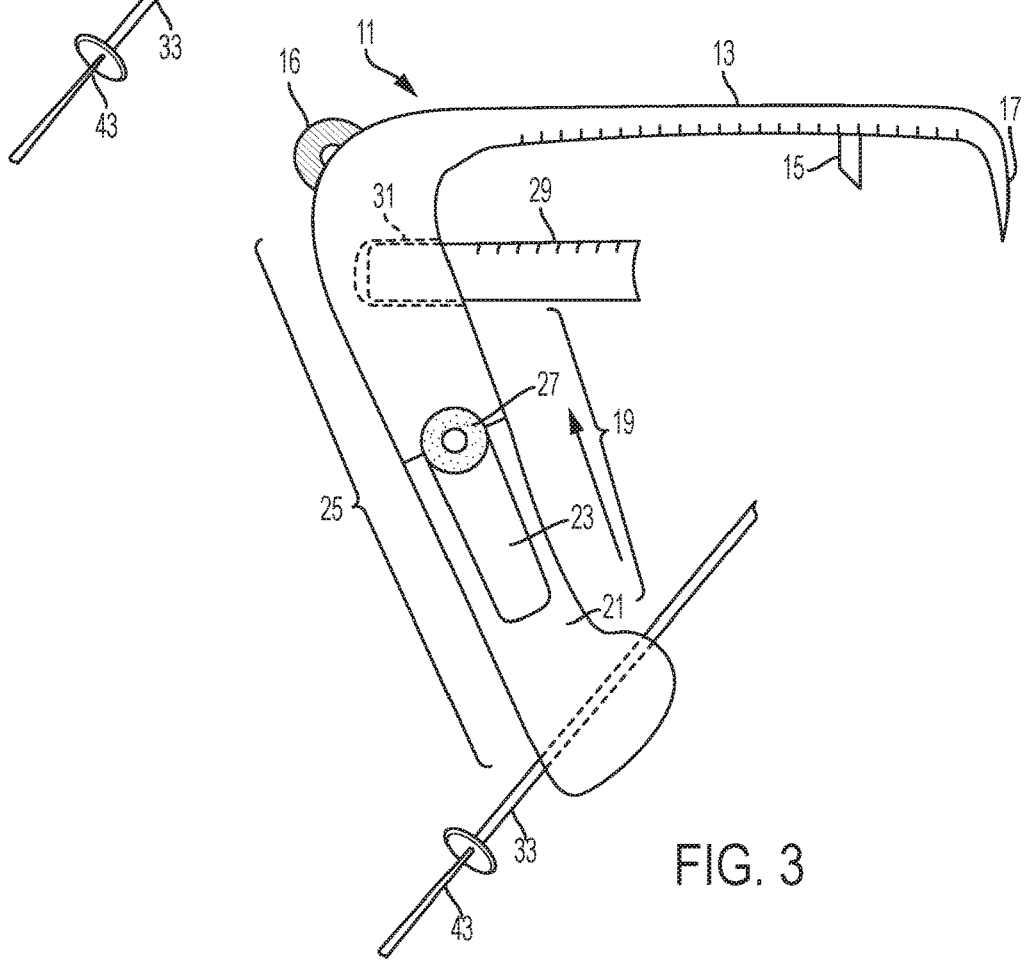
FIG. 3 is a schematic side view of an adjustable device in a contracted configuration in accordance with embodiment.

FIGS. 2 and 3 illustrate additional exemplary embodiments of the adjustable device 11 of the present invention, with the addition of an outer portion of the second arm 21, inner portion of the second arm 23, second arm adjustment means 27, guiding device 33, and guide pin 43. The remaining elements illustrated in FIGS. 2 and 3 are substantially similar in form and function as those disclosed herein in FIG. 1.

FIG. 2 illustrates an exemplary embodiment of the adjustable device 11 in a protracted position. The inner portion of the second arm 23 engages the outer portion of the second arm 21 on two surfaces. However, this is not required, and the inner portion of the second arm 23 may be completely enveloped by the outer portion of the second arm 21 or the inner portion 23 may engage the outer portion 21 on more or fewer than two surfaces. Additionally, though the inner portion of the second arm 23 is depicted in FIG. 2 as being disposed superiorly to the outer portion of the second arm 21, this is not required. For example, the outer portion of the second arm 21 may be disposed superiorly to the inner portion of the second arm 23 in alternative embodiments.

The inner portion of the second arm 23 and outer portion of the second arm 21 are configured to move relative to each other. This may be accomplished in a variety of ways, such as, for example, by ratcheting or sliding. For example, in FIG. 2, the inner portion of the second arm 23 is configured to slide within the outer portion of the second arm 21 such that a length of second arm 25 is adjusted by changing the magnitude of overlap between the two portions of the second arm 19. That is, further sliding the inner portion of the second arm 23 within the outer portion of the second arm 21 will increase the amount that the two portions overlap and shorten the length of second arm 25.

In FIGS. 2 and 3, the second arm 19 further comprises second arm adjustment means 27 that is configured to move the inner portion of the second arm 23 and the outer portion of the second arm 21 relative to each other. The second arm adjustment means 27 is depicted as a knob in FIGS. 2 and 3. Also, in FIGS. 2 and 3, the second arm adjustment means 27 is disposed on the inner portion of the second arm 23 such that a user can grab or otherwise engage the second arm adjustment means 27 and slide the inner portion of the second arm 23 within the outer portion of the second arm 21. It should be appreciated that this adjustment may be accomplished without any additional tools.

Those skilled in the art will appreciate that the second arm adjustment means 27 may be in any form suitable to move the inner portion of the second arm 23 and the outer portion of the second arm 21 relative to each other. For example, the second arm adjustment means 27 may be a button, dial, ratchet, switch, notch, or suitable equivalents thereof. The second arm adjustment means 27 may be manually or electrically operated. For example, the second arm adjustment means 27 may be coupled to a motor that is coupled to the inner portion of the second arm 23, or the outer portion of the second arm 21, or another portion of the second arm 19. This motor may be powered using a battery, inductive power, or directly through a power cord. However, this is not required, and the second arm adjustment means 27 may be directly coupled to one or more portions of the second arm 19 such that the length of the second arm 25 may be manually adjusted without the use of electronic means.

FIGS. 2 and 3 further depict a guiding device 33 disposed on an inferior portion of the second arm 19. The guiding device 33 is configured to engage and lay flush against a surface of an anatomic structure. For example, as depicted in FIG. 4, the guiding device 33 may engage and lay flush against an anterior surface of a tibia 51.

The guiding device 33 may be further configured to receive a guide pin 43. The guide pin 43 may be 3/32 of an inch in diameter, but this is not required, and those skilled in the art will appreciate that a differently sized guide pin 43 may be required and utilized as operational or situational demands dictate.

FIG. 3 further illustrates an exemplary embodiment of the adjustable device 11 in a contracted state. FIG. 3 is provided to illustrate the adjustability of the length of the second arm 25. Comparing FIG. 3 with FIG. 2, the inner portion of the second arm 23 has been slid within the outer portion of the second arm 21 so as to maximize the magnitude of overlap between the two portions of the second arm 19. Accordingly, FIG. 3 depicts the length of the second arm 25 in its shortest configuration.

It should be appreciated that embodiments of the adjustable device 11, such as those depicted in FIGS. 2 and 3, can be easily adjusted. The second arm adjustment means 27 can be utilized to quickly and simply adjust the length of the second arm 25. In other words, the current invention allows a user to change between a protracted state (e.g., as depicted in FIG. 2) and a contracted state (e.g., as depicted in FIG. 3), and vice versa. Moreover, this adjustment may be accomplished without the use of additional tools.

It should also be appreciated that FIGS. 2 and 3 show only exemplary configurations that are not limiting. That is, the adjustable device 11 may be configured such that the length of the second arm 25 may be any length in the range of those depicted in FIGS. 2 and 3.

Moreover, though FIGS. 2 and 3 depict exemplary configurations of the inner portion of the second arm 23 and the outer portion of the second arm 21, these are not meant to limit the possible ranges of motion of the portions of the second arm 19 nor are they intended to limit the range of possible lengths of the second arm 25. Alternative embodiments of the present invention may allow for a length of the second arm 25 outside of the range depicted in FIGS. 2 and 3. Adjusting the adjustable device 11 to allow for a length of the second arm 25 outside of the range depicted in FIGS. 2 and 3 would be within the context of the embodiments disclosed herein to meet the operational or situational demands dictated by use of the adjustable device 11.

FIG. 4 further illustrates an exemplary embodiment of the adjustable device 11 in a configuration that may be seen in an exemplary use of the present invention. A first arm 13 terminates in a curved hook 17 that engages a reference structure 35. In FIG. 4, the curved hook 17 engages a posterior region of a tibial plateau. The curved hook 17 is aligned with a measurement member 29 that rests against an anterior edge of a tibial plateau such that the curved hook 17 and measurement member 29 simultaneously engage opposing ends of the tibial plateau. With both ends of the tibial plateau engaged, a total distance across the anatomic structure 41 can be determined by, for example and without limitation, reading the measurement by aligning graduated markings on the measurement member 29 and first arm 13. The total distance across the anatomic structure 41 may also be read with the assistance of arthroscopic devices or techniques, though these are not required. It should be appreciated that neither fluoroscopy nor other imaging techniques are required to determine or read the total distance across the anatomic structure 41.

In FIG. 4, the targeting arm 15 is depicted as having engaged the surface of the tibial plateau at a target distance across the anatomic structure 39. The target distance across the anatomic structure 39 may be calculated by referencing a target percentage across the anterior-posterior distance of the anatomic structure. For example, and without limitation, the target percentage across the anatomic structure may be 35%. In these non-limiting embodiments, the anterior edge of the anatomic structure may correspond to 0% and the posterior edge of the anatomic structure may correspond to 100%. In some embodiments, the target distance across the anatomic structure 39 may be calculated by multiplying the total distance across the anatomic structure 41 by the target percentage across the anterior-posterior distance of the anatomic structure.

Though not depicted in FIG. 4, additional arthroscopic devices, apparatuses, and techniques may be utilized to aid in the adjustment of the target arm 15. However, these are not required, and it should be appreciated that the targeting arm 15 may be adjusted to engage the anatomic structure at the target distance across the anatomic structure 39 without the use of additional tools.

Though not depicted in FIG. 4, the target location for the bone tunnel 45 may be marked using conventional devices and techniques. For example, and without limitation, an electrocautery device, surgical pen, or microfracture awl may be used to mark where the targeting arm 15 engages an anatomic structure at the target distance across the anatomic structure 39. Other techniques and devices may also be employed, and identification of equivalents would be within the skill of an ordinary practitioner. However, this step is not required, and in other embodiments of the present invention the target location for the bone tunnel 45 may not be marked.

In FIG. 4, a guiding device 33 engages an anterior surface of a tibia 51 in accordance with the position of the targeting arm 15. The length of the second arm 25 may be adjusted in accordance with the position of the targeting arm 15 by utilizing the second arm adjustment means 27 to slide the inner portion of the second arm 23 within the outer portion of the second arm 21 such that the guiding device is aligned with the position of the targeting arm 15. Those skilled in the art will appreciate that this adjustment may be made with the assistance of arthroscopic tools, apparatuses, or techniques, but these are not required. Accurately adjusting the length of the second arm 25 in accordance with the position of the targeting arm 15 may be accomplished using available computations and adjustments to achieve a reliable and precise calibration.

The guiding device 33 may be configured to receive a guide pin 43. This guide pin 43 may be inserted in to an anterior surface of the tibia 51 to mark the path of a bone tunnel 45 that may be drilled using a cannulated drill, reamer, or other conventional surgical tool, device, instrument, or technique. It should be appreciated that other complimentary tools, devices, instruments, and materials may be implemented and employed within the context of various embodiments other than the guiding device and guide pin.

FIG. 5 further illustrates an exemplary embodiment of the adjustable device 11 in a configuration that may be seen in an exemplary use of the present invention. A first arm 13 passes under a femur 53 and terminates in a curved hook 17 that engages a reference structure 35. In FIG. 5, the reference structure 35 is a posterior edge of a tibial plateau.

As in FIG. 4, FIG. 5 depicts a targeting arm 15 engaging a tibial plateau at a target distance across the anatomic structure 39. The adjustment of the targeting arm 15 may be accomplished using the targeting arm adjustment means 16.

Though not depicted in FIG. 5, additional arthroscopic devices, apparatuses, and techniques may be utilized to aid in the adjustment of the target arm 15. However, it should be appreciated that the targeting arm 15 may be adjusted to engage the anatomic structure at the target distance across the anatomic structure 39 without the use of additional tools.

In FIG. 5, a second arm 19 terminates in a curved and planar configuration that is configured to engage and rest against a surface of an anatomic structure. For example, as depicted in FIG. 5, the second arm 19 may rest against an anterior surface of a tibia 51. However, this is not required. The second arm 19 may alternatively terminate in a manner such that it does not rest against a surface of an anatomic structure. For example, the second arm 19 may terminate in a handle that allows a user to grasp and control the adjustable device 11 during operation.

FIG. 5 additionally depicts an operational or strategic location for a bone tunnel 45 based upon the target distance across the anatomic structure 39 as engaged by the targeting arm 15. Though not depicted in FIG. 5, the operational or strategic exit point of the bone tunnel 45 (as engaged by the targeting arm 15 in FIG. 5) may be marked using conventional surgical techniques and devices. For example, an electrocautery device, surgical pen, or microfracture awl may be utilized for this purpose. Once the target distance across the anatomic structure 39 is identified in accordance to the aspects of various embodiments of the present invention disclosed herein, placing a bone tunnel 45 directed to the target distance across the anatomic structure 39 would be well within the skill of an ordinary artisan. Available tibial tunnel placement guides, such as the Acufex Director, may be utilized to drill a bone tunnel 45 to the target location engaged by the targeting arm 15. However, this is not required, and additional embodiments of the present invention (such as those depicted in FIG. 4) provide for a device that can both identify the target location for a bone tunnel and provide a guiding device 33 for placing a guide pin 43 that can then identify the path of a bone tunnel 45.

Figure 6:
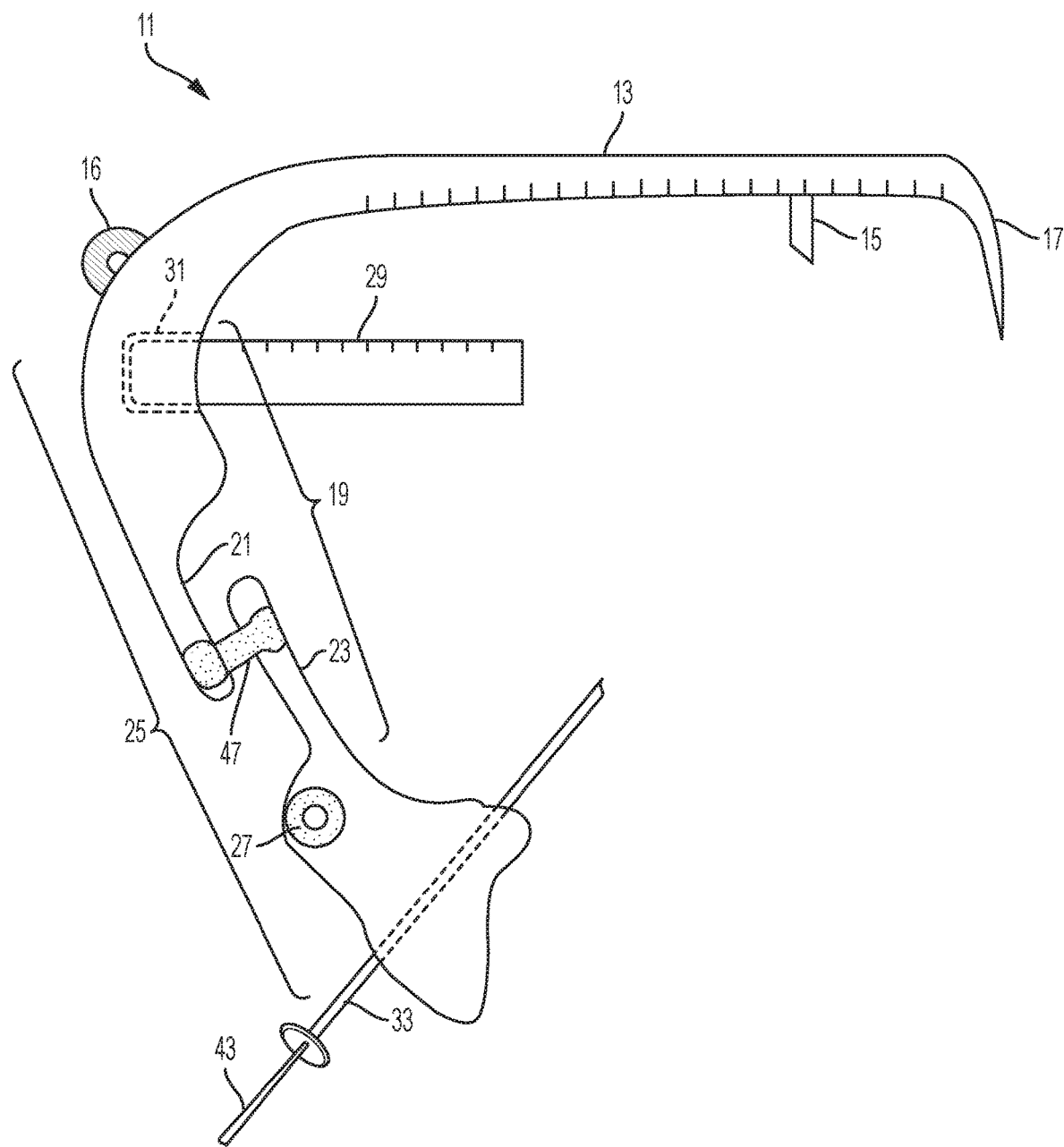
FIG. 6 is a schematic side view of an adjustable device in accordance with an embodiment.

FIG. 6 depicts an additional embodiment of the adjustable device 11 of the present invention. In FIG. 6, the inner portion of the second arm 23 and the outer portion of the second arm 21 are separated by a means to separate the second arm 47. The means to separate the second arm 47 is configured to allow the inner portion of the second arm 23 and outer portion of the second arm 21 to move relative to each other so as to adjust a length of the second arm 25.

Those skilled in the art will appreciate that the means to separate the second arm 47 may be of any form suitable to separate the inner portion of the second arm 23 and the outer portion of the second arm 21. For example, in some non-limiting embodiments, the means to separate the second arm 47 may be, but is not limited to, a bracket, clamp, guide, bridge, or suitable equivalents thereof. FIG. 6 depicts the means to separate the second arm 47 as a bracket with ends that completely envelop respective regions of the portions of the second arm 19. However, this is not required. For example, the means to separate the second arm 47 may engage a portion of one or both of the portions of the second arm 19 on one or more of their respective surfaces, or the means to separate the second arm 47 may envelop a smaller portion of the respective portions of the second arm 19. In some embodiments, the means to separate the second arm 47 may remain in a fixed position, and in other embodiments the means to separate the second arm 47 may move relative to one or both of the inner portion of the second arm 23 and the outer portion of the second arm 21.

FIG. 6 further depicts a second arm adjustment means 27 disposed on an inferior portion of the second arm. However, this is not required, and the second arm adjustment means 27 may be disposed on any surface of the adjustable device 11, such as, for example, on a superior region on the second arm 19. Alternatively, the second arm adjustment means 27 may be disposed on the inner portion of the second arm 23, the outer portion of the second arm 21, or the means to separate the second arm 47.

The additional elements of the adjustable device 11 as depicted in FIG. 6 are substantially similar in form and function as those disclosed and depicted in FIGS. 2, 3, and 4.

Figure 7:
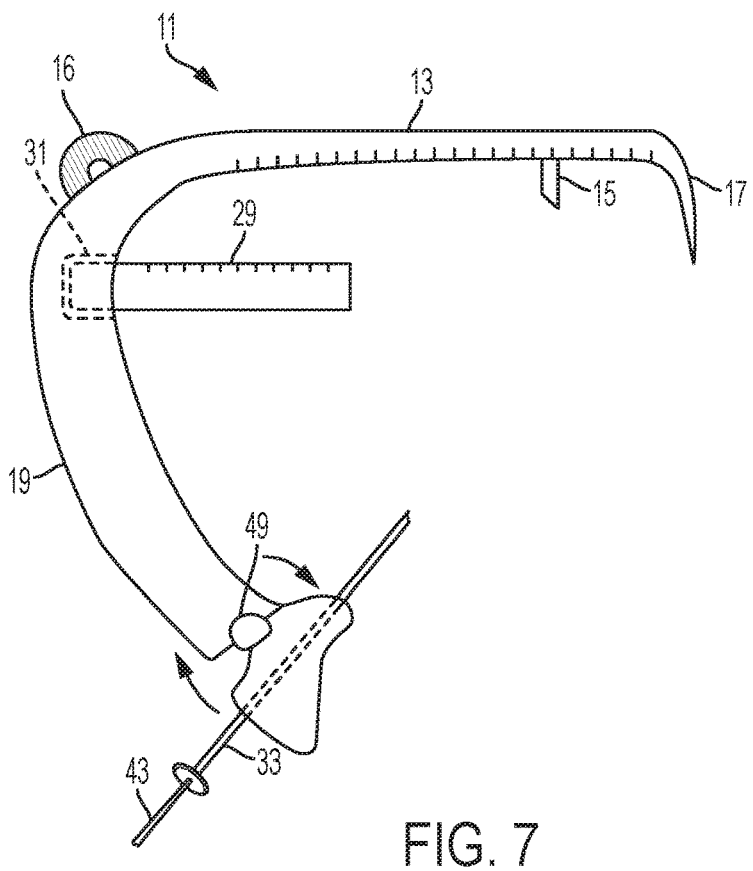
FIG. 7 is a schematic side view of an adjustable device in a "steep angle" configuration in accordance with an embodiment.
Figure 8:
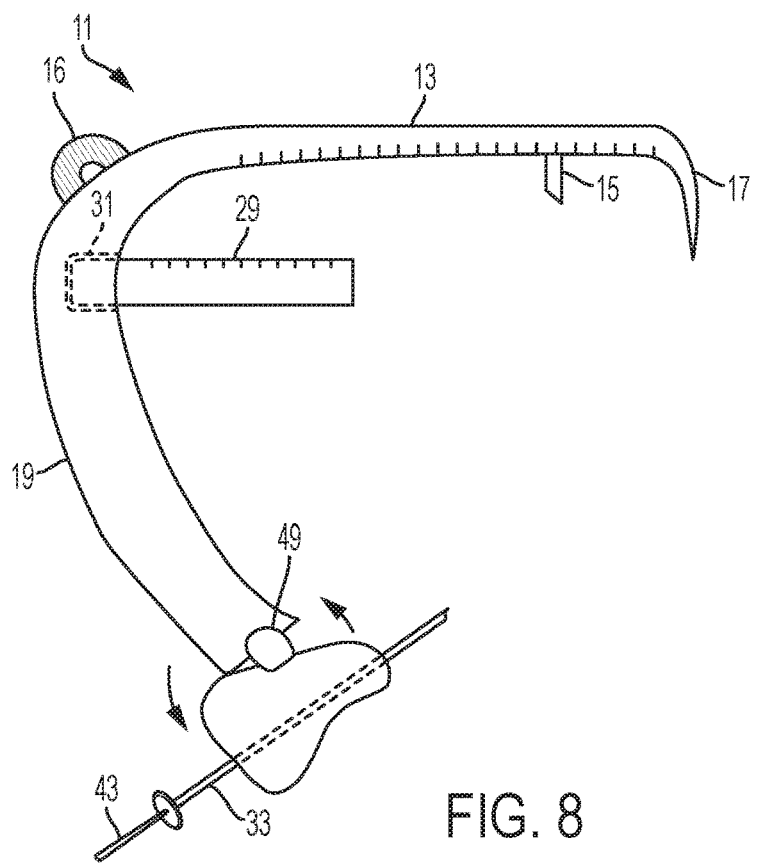
FIG. 8 is a schematic side view of an adjustable device in a "shallow angle" configuration in accordance with an embodiment.

FIGS. 7 and 8 illustrate additional exemplary embodiments of the adjustable device 11 of the present invention. An adjustable guiding device 33 is disposed on an inferior portion of the second arm 19.

In FIG. 7, the adjustable guiding device 33 is configured to pivot about a guiding device adjustment means 49 disposed on an inferior portion of the second arm 19. The guiding device adjustment means 49 is configured to allow the guiding device 33 to pivot, rotate, translate, or otherwise move about a point on the second arm 19 so as to adjust the angle of the guiding device 33 with respect to the second arm 19.

It should be appreciated that the guiding device adjustment means 49 may be of any form suitable to allow the guiding device 33 to move relative to the second arm 19. For example, the guiding device adjustment means 49 may be, but is not limited to, a knob, dial, button, switch, ratchet, nut, bolt, hinge, ball and socket joint, or suitable equivalents thereof.

FIG. 7 depicts the adjustable device 11 in a configuration where the guiding device 33 is oriented at a steep angle with respect to the second arm 19. Such a configuration may be advantageous in situations where the target location for bone tunnel placement is located on a substantially anterior region of the target anatomy.

FIG. 8 depicts the adjustable device 11 in a configuration where the guiding device 33 is oriented at a shallow angle with respect to the second arm 19. As compared to the configuration depicted in FIG. 7, this adjustment is possible by, for example, rotating the guiding device 33 about the guiding device adjustment means 49. Such a configuration may be advantageous in situations where the target location for bone tunnel placement is located on a more posterior region of the target anatomy, as compared with the configuration depicted in FIG. 7.

It should be appreciated that embodiments of the adjustable device 11, such as those depicted in FIGS. 7 and 8, can be easily adjusted. The guiding device adjustment means 49 can be utilized to quickly and simply adjust the angle of guiding device 33 with respect to the second arm 19. In other words, an aspect of an embodiment of the invention allows a user to change between a steep angle configuration (e.g., as depicted in FIG. 7) and a shallow angle configuration (e.g., as depicted in FIG. 8), and vice versa. Moreover, this adjustment may be accomplished without the use of additional tools.

It should also be appreciated that FIGS. 7 and 8 show only exemplary configurations that are not limiting. That is, the angle of the guiding device 33 with respect to the second arm 19 may be any angle in the range of those depicted in FIGS. 7 and 8. The guiding device 33 may be configured to pivot, rotate, translate or otherwise move in any continuous or iterative manner about the guiding device adjustment means 49. For example, and without limitation, the guiding device 33 may slide, rotate continuously, or ratchet.

Moreover, though FIGS. 7 and 8 depict exemplary angles at the limits of the depicted range of motion, these are not meant to be limiting. Alternative embodiments of the present invention may allow for angles of the guiding device 33 with respect to the second arm 19 outside of the range depicted in FIGS. 7 and 8. Adjusting the adjustable device 11 to allow for more extreme angles would be within the context of the embodiments disclosed herein to meet the operational or situational demands dictated by use of the adjustable device 11.

The additional elements of the adjustable device 11 as depicted in FIGS. 7 and 8 are substantially similar in form and function as those disclosed and depicted in FIGS. 1 and 5.

The adjustable device 11 as shown and depicted in FIGS. 1-8 may be constructed of a number of suitable materials. Such materials may include, for example, surgical-grade stainless steel, titanium, aluminum, or plastic polymers. Other materials would also be suitable. Identification of equivalents is well within the skill of the ordinary practitioner and would require no more than routine experimentation. It should be appreciated that the adjustable device 11 may be composed of such materials in part or in whole.

Further, it should be appreciated that an embodiment may have additional uses in addition to those heretofore disclosed and discussed. For example, the present invention may be used to identify a target location for one or more bone tunnels during reconstructive procedures involving other structures of the knee, such as the posterior cruciate ligament (PCL), the medial collateral ligament (MCL), or the lateral collateral ligament (LCL). It should also be appreciated that embodiments may be implemented and directed at other target areas or intended areas of the subject in addition to those disclosed and discussed. The present invention has a broad application in the field of orthopedic surgery and may be utilized in any setting wherein a target location for a bone tunnel is identified. For example, embodiments of the present invention may be utilized during reconstructive procedures of the shoulder, ankle, or elbow.

Of course, it should be understood that a wide range of changes and modifications may be made to the preferred embodiment described above. It is therefore intended that the foregoing detailed description be regarded as illustrative rather than limiting, and that it be understood that it is the following claims, including all equivalents, which are intended to define the scope of this invention.

EXAMPLES

Practice of an aspect of an embodiment (or embodiments) of the invention will be still more fully understood from the following examples and experimental results, which are presented herein for illustration only and should not be construed as limiting the invention in any way.

Example 1

An adjustable device for identifying a target location for a bone tunnel of a subject. The device may comprise: a first arm comprising an anterior portion and a posterior portion opposite said anterior portion, wherein said posterior portion is configured to engage a reference structure; a targeting arm movably disposed on said first arm; wherein said targeting arm is configured to extend toward and engage across a region of an anatomic structure; a second arm comprising a superior portion and an inferior portion opposite said superior portion, wherein said superior portion of said second arm is in communication with said anterior portion of said first arm; and a measurement member slidably disposed on said second arm, wherein said measurement member and said second arm are configured to move relative to each other, and wherein said measurement member is configured to extend toward and engage a surface of the anatomic structure.

Example 2

The device in example 1, further comprising a targeting arm adjustment means disposed on said device, wherein said targeting arm adjustment means is configured to move said targeting arm relative to said first arm.

Example 3

The device in example 1 (as well as subject matter in whole or in part of example 2), wherein said targeting arm is further configured to slide along said first arm.

Example 4

The device in example 1 (as well as subject matter of one or more of any combination of examples 2-3, in whole or in part), wherein said targeting arm is configured to pivot about a fixed point on said first arm.

Example 5

The device in example 1 (as well as subject matter of one or more of any combination of examples 2-4, in whole or in part), wherein said targeting arm is further configured to withdraw and lay flush against a surface of said first arm.

Example 6

The device in example 1 (as well as subject matter of one or more of any combination of examples 2-5, in whole or in part), further comprising a guiding device disposed on said inferior portion of said second arm, wherein said guiding device is configured to receive a guide pin.

Example 7

The device in example 1 (as well as subject matter of one or more of any combination of examples 2-6, in whole or in part), wherein said second arm is convexly curved.

Example 8

The device in example 1 (as well as subject matter of one or more of any combination of examples 2-7, in whole or in part), wherein said inferior portion of said second arm is further configured to engage a surface of the anatomic structure.

Example 9

The device in example 1 (as well as subject matter of one or more of any combination of examples 2-8, in whole or in part), wherein the bone tunnel is a tibial bone tunnel.

Example 10

The device in example 1 (as well as subject matter of one or more of any combination of examples 2-9, in whole or in part), wherein said first arm further comprises a plurality of graduated markings indicating units of length.

Example 11

The device in example 1 (as well as subject matter of one or more of any combination of examples 2-10, in whole or in part), wherein said measurement member further comprises a plurality of graduated markings indicating units of length.

Example 12

The device in example 1 (as well as subject matter of one or more of any combination of examples 2-11, in whole or in part), wherein said posterior portion of said first arm terminates in a curved hook, wherein said curved hook is configured to engage said reference structure.

Example 13

The device in example 1 (as well as subject matter of one or more of any combination of examples 2-12, in whole or in part), wherein the reference structure is a posterior cruciate ligament.

Example 14

The device in example 1 (as well as subject matter of one or more of any combination of examples 2-13, in whole or in part), wherein the reference structure is a posterior end of a tibial plateau.

Example 15

The device in example 1 (as well as subject matter of one or more of any combination of examples 2-14, in whole or in part), wherein the region of the anatomic structure is a tibial plateau.

Example 16

The device in example 1 (as well as subject matter of one or more of any combination of examples 2-15, in whole or in part), wherein said targeting arm may be further configured to engage the anatomic structure at a target distance across the anatomic structure. Further, said target distance corresponds to a predetermined percentage across the total distance across the anatomic structure, wherein said target distance is calculated in reference to said predetermined percentage and said total distance across the anatomic structure.

Example 17

The device in example 1 (as well as subject matter of one or more of any combination of examples 2-16, in whole or in part), wherein said second arm may further comprise an outer portion of said second arm, an inner portion of said second arm in communication with at least one surface of said outer portion, and a second arm adjusting means disposed on said second arm. Further, wherein said second arm adjusting means is configured to alter a length of said second arm by slidably moving said inner portion of said second arm and said outer portion of said second arm relative to each other.

Example 18

The device in example 17 (as well as subject matter of one or more of any combination of examples 2-16, in whole or in part), further comprising a means to separate said outer portion of said second arm and said inner portion of said second arm, wherein said outer portion of said second arm is offset from said inner portion of said second arm, and wherein said means to separate said outer portion of said second arm and said inner portion of said second arm is configured to allow said outer portion of said second arm and said inner portion of said second arm to move relative to each other.

Example 19

The device in example 17 (as well as subject matter of one or more of any combination of examples 2-16 and 18, in whole or in part), wherein said outer portion of said second arm completely envelops said inner portion of said second arm.

Example 20

The device in example 17 (as well as subject matter of one or more of any combination of examples 2-16 and 18-19, in whole or in part), wherein said outer portion of said second arm is disposed superiorly to said inner portion of said second arm.

Example 21

The device in example 17 (as well as subject matter of one or more of any combination of examples 2-16 and 18-20, in whole or in part), wherein said outer portion of said second arm is disposed inferiorly to said inner portion of said second arm.

Example 22

The device in example 6 (as well as subject matter of one or more of any combination of examples 1-5 and 7-21, in whole or in part), wherein said guiding device further comprises a guiding device adjustment means disposed on said guiding device, wherein said guiding device adjustment means is configured to adjust the angle of said guiding device relative to said second arm.

Example 23

The device in example 22 (as well as subject matter of one or more of any combination of examples 2-21, in whole or in part), wherein said guiding device is further configured to rotate about a fixed point on said inferior portion of said second arm.

Example 24

The device in example 1 (as well as subject matter of one or more of any combination of examples 2-23, in whole or in part), wherein said second arm further comprises a slot, wherein said slot is configured to accommodate said measurement member.

Example 25

The device in example 24 (as well as subject matter of one or more of any combination of examples 2-23, in whole or in part), wherein said measurement member is further configured to slidably move within said slot.

Example 26

The device in example 24 (as well as subject matter of one or more of any combination of examples 2-23 and 25, in whole or in part), wherein said second arm further comprises a measurement member adjustment means disposed on said second arm, wherein said measurement member adjustment means is configured to slidably adjust said measurement member within said slot.

Example 27

The device in example 24 (as well as subject matter of one or more of any combination of examples 2-23 and 25-26, in whole or in part), wherein said measurement member further comprises a measurement member adjustment means disposed on said measurement member, wherein said measurement member adjustment means is configured to slidably adjust said measurement member within said slot.

Example 28

The device in example 6 (as well as subject matter of one or more of any combination of examples 1-5 and 7-27, in whole or in part), wherein said guide pin has a diameter of $3/32$ of an inch. It should be noted that the diameter of the guide pin (or other tool or device) may be larger or smaller as desired.

Example 29

The device in example 1 (as well as subject matter of one or more of any combination of examples 2-28, in whole or in part), wherein said adjustable device is composed of a material selected from the group consisting of surgical-grade stainless steel, titanium, aluminum, or plastic. It should be noted that other materials may be appropriate, and the device may be constructed of such materials in whole or in part.

Example 30

A method for identifying a target location for a bone tunnel in a subject. The method may comprise utilizing an adjustable device to engage a reference structure of said subject; utilizing a measurement member of said adjustable device to measure a total distance across a region of an anatomic structure of said subject; calculating a target distance across the region of the anatomic structure of said subject based upon a predetermined target percentage across said total distance; and engaging the anatomic structure at said target distance across the region of the anatomic structure by adjusting a targeting arm that is movably disposed on a first arm of said adjustable device.

Example 31

The method of example 30, further comprising the step of marking said target distance across the region of the anatomic structure.

Example 32

The method of example 30 (as well as subject matter in whole or in part of example 31), further comprising the step of moving said measurement member such that said measurement member is advanced toward a surface of the anatomic structure.

Example 33

The method of example 30 (as well as subject matter of one or more of any combination of examples 31-32, in whole or in part), further comprising the step of moving said measurement member such that said measurement member engages a surface of the anatomic structure.

Example 34

The method of example 30 (as well as subject matter of one or more of any combination of examples 31-33, in whole or in part), further comprising the step of adjusting a second arm of said adjustable device in accordance with the position of said targeting arm.

Example 35

The method of example 34 (as well as subject matter of one or more of any combination of examples 31-33, in whole or in part), wherein said adjusting includes altering the length of said second arm.

Example 36

The method of example 34 (as well as subject matter of one or more of any combination of examples 31-33 and 35, in whole or in part), further comprising the step of adjusting a guiding device disposed on an inferior portion of said second arm in accordance with the position of said targeting arm; wherein said guiding device is configured to rotate about a fixed point on an inferior portion of said second arm.

Example 37

The method of example 34 (as well as subject matter of one or more of any combination of examples 31-33 and 35-36, in whole or in part), further comprising adjusting an angle of a guiding device that is disposed on an inferior portion of said second arm wherein said guiding device is angled to correspond with the position of said targeting arm.

Example 38

The method of example 34 (as well as subject matter of one or more of any combination of examples 31-33 and 35-37, in whole or in part), further comprising the step of inserting a guide pin through a guiding device disposed on an inferior portion of said second arm.

Example 39

The method of example 38 (as well as subject matter of one or more of any combination of examples 31-37, in whole or in part), further comprising the step of drilling a bone tunnel at the location of the guide pin insertion.

Example 40

The method of example 30 (as well as subject matter of one or more of any combination of examples 31-39, in whole or in part), further comprising the steps of removing the adjustable device and utilizing a tibial tunnel guide device to engage said region of the anatomic structure at said target distance.

Example 41

The method of example 40 (as well as subject matter of one or more of any combination of examples 31-39, in whole or in part), further comprising the steps of inserting a guide pin in said anatomic structure using said tibial tunnel guide device and drilling a bone tunnel.

Example 42

The method of example 30 (as well as subject matter of one or more of any combination of examples 31-41, in whole or in part), wherein the bone tunnel is a tibial tunnel.

Example 43

The method of example 30 (as well as subject matter of one or more of any combination of examples 31-42, in whole or in part), wherein the reference structure is a posterior cruciate ligament.

Example 44

The method of example 30 (as well as subject matter of one or more of any combination of examples 31-43, in whole or in part), wherein the reference structure is a posterior end of a tibial plateau.

Example 45

The method of example 30 (as well as subject matter of one or more of any combination of examples 31-44, in whole or in part), wherein the region of the anatomic structure is a tibial plateau.

Example 46

The method of example 30 (as well as subject matter of one or more of any combination of examples 31-45, in whole or in part), wherein the predetermined target percentage is 35% and wherein said anterior end of the region of the anatomic structure corresponds to 0% and said posterior end of the region of the anatomic structure corresponds to 100%.

Example 47

The method of manufacturing any of the devices (or their components and subcomponents) provided in any one or more of examples 1-29.

Example 48

The method of using any of the devices (or their components and subcomponents) provided in any one or more of examples 1-29.

Example 49

A system including any of the devices (or their components and subcomponents) provided in any one or more of examples 1-29.

Example 50

A kit including any of the devices (or their components and subcomponents) provided in any one or more of examples 1-29.

REFERENCES

The devices, systems, apparatuses, compositions, materials, machine readable media, computer program products, and methods of various embodiments of the invention disclosed herein may utilize aspects disclosed in the following references, applications, publications and patents and which are hereby incorporated by reference herein in their entirety, and which are not admitted to be prior art with respect to the present invention by inclusion in this section:

1. Matava M J, Arciero R A, Baumgarten K M, et al. Multirater Agreement of the Causes of Anterior Cruciate Ligament Reconstruction Failure: A Radiographic and Video Analysis of the MARS Cohort. Am J Sports Med 2014.

2. Morgan J A, Dahm D, Levy B, Stuart M J, MARS Study Group. Femoral tunnel malposition in ACL revision reconstruction. J Knee Surg 2012; 25:361-368.

3. Sommer C, Friederich N F, Muller W. Improperly placed anterior cruciate ligament grafts: correlation between radiological parameters and clinical results. Knee Surg Sports Traumatol Arthrosc 2000; 8: 207-213.

4. Tompkins M, Milewski M D, Brockmeier S F, Gaskin C M, Hart J M, Miller M D. Anatomic femoral tunnel drilling in anterior cruciate ligament reconstruction: use of an accessory medial portal versus traditional transtibial drilling. Am J Sports Med 2012; 40:1313-1321.

5. Seon J K, Park S J, Lee K B, Seo H Y, Kim M S, Song E K. In vivo stability and clinical comparison of anterior cruciate ligament reconstruction using low or high femoral tunnel positions. Am J Sports Med 2011; 39:127-133.

6. Steiner M E, Battaglia T C, Heming J F, Rand J D, Festa A, Baria M. Independent drilling outperforms conventional transtibial drilling in anterior cruciate ligament reconstruction. Am J Sports Med 2009; 37:1912-1919.

7. Harner C D, Honkamp N J, Ranawat A S. Anteromedial portal technique for creating the anterior cruciate ligament femoral tunnel. Arthroscopy 2008; 24:113-115.

8. Pinczewski L A, Salmon L J, Jackson W F, von Bormann R B, Haslam P G, Tashiro S. Radiological landmarks for placement of the tunnels in single-bundle reconstruction of the anterior cruciate ligament. J Bone Joint Surg Br 2008; 90:172-179.

9. Staubli H U, Rauschning W. Tibial attachment area of the anterior cruciate ligament in the extended knee position. Anatomy and cryosections in vitro complemented by magnetic resonance arthrography in vivo. Knee Surg Sports Traumatol Arthrosc 1994; 2:138-146.

10. Amis A A, Jakob R P. Anterior cruciate ligament graft positioning, tensioning and twisting. Knee Surg Sports Traumatol Arthrosc 1998; 6 Suppl 1:S2-12.

11. Bedi A, Maak T, Musahl V, et al. Effect of tibial tunnel position on stability of the knee after anterior cruciate ligament reconstruction: is the tibial tunnel position most important? Am J Sports Med 2011; 39:366-373.

12. Howell S M, Clark J A. Tibial tunnel placement in anterior cruciate ligament reconstructions and graft impingement. Clin Orthop Relat Res 1992; (283):187-195.

13. Kasten P, Szczodry M, Irrgang J, Kropf E, Costello J, Fu F H. What is the role of intra-operative fluoroscopic measurements to determine tibial tunnel placement in anatomical anterior cruciate ligament reconstruction? Knee Surg Sports Traumatol Arthrosc 2010; 18:1169-1175.

14. Wolf B R, Ramme A J, Wright R W, et al. Variability in ACL tunnel placement: observational clinical study of surgeon ACL tunnel variability. Am J Sports Med 2013; 41:1265-1273.

15. Hatayama K, Terauchi M, Saito K, Higuchi H, Yanagisawa S, Takagishi K. The importance of tibial tunnel placement in anatomic double-bundle anterior cruciate ligament reconstruction. Arthroscopy 2013; 29:1072-1078.

16. Moloney G, Araujo P, Rabuck S, et al. Use of a fluoroscopic overlay to assist arthroscopic anterior cruciate ligament reconstruction. Am J Sports Med 2013; 41:1794-1800.

17. Lorenz S, Elser F, Mitterer M, Obst T, Imhoff A B. Radiologic evaluation of the insertion sites of the 2 functional bundles of the anterior cruciate ligament using 3-dimensional computed tomography. Am J Sports Med 2009; 37: 2368-2376.

18. Larson B J, Egbert J, Goble E M. Radiation exposure during fluoroarthroscopically assisted anterior cruciate reconstruction. Am J Sports Med 1995; 23:462-464.

19. Hughes A W, Dwyer A J, Govindaswamy R, Lankester B. The use of intra-operative fluoroscopy for tibial tunnel placement in anterior cruciate ligament reconstruction. Bone Joint Res 2012; 1:234-237.

20. Jackson D W, Gasser S I. Tibial tunnel placement in ACL reconstruction. Arthroscopy 1994; 10:124-131.

21. Ziegler C G, Pietrini S D, Westerhaus B D, et al. Arthroscopically pertinent landmarks for tunnel positioning in single-bundle and double-bundle anterior cruciate ligament reconstructions. Am J Sports Med 2011; 39:743-752.

22. Morgan C D, Kalman V R, Grawl D M. Definitive landmarks for reproducible tibial tunnel placement in anterior cruciate ligament reconstruction. Arthroscopy 1995; 11:275-288.

23. Forsythe B, Kopf S, Wong A K, et al. The location of femoral and tibial tunnels in anatomic double-bundle anterior cruciate ligament reconstruction analyzed by three-dimensional computed tomography models. J Bone Joint Surg Am 2010; 92: 1418-1426.

24. Kondo E, Merican A M, Yasuda K, Amis A A. Biomechanical analysis of knee laxity with isolated anteromedial or posterolateral bundle-deficient anterior cruciate ligament. Arthroscopy 2014; 30:335-343.

25. Amis A A, Dawkins G P. Functional anatomy of the anterior cruciate ligament. Fibre bundle actions related to ligament replacements and injuries. J Bone Joint Surg Br 1991; 73:260-267.

26. Amis A A. The functions of the fibre bundles of the anterior cruciate ligament in anterior drawer, rotational laxity and the pivot shift. Knee Surg Sports Traumatol Arthrosc 2012; 20:613-620.

27. Howell S M, Clark J A, Farley T E. A rationale for predicting anterior cruciate graft impingement by the intercondylar roof. A magnetic resonance imaging study. Am J Sports Med 1991; 19:276-282.

28. Howell S M. Arthroscopic roofplasty: a method for correcting an extension deficit caused by roof impingement of an anterior cruciate ligament graft. Arthroscopy 1992; 8:375-379.

29. Astur D C, Santos C V, Aleluia V, et al. Characterization of cruciate ligament impingement: the influence of femoral or tibial tunnel positioning at different degrees of knee flexion. Arthroscopy 2013; 29:913-919.

30. Iriuchishima T, Yorifuji H, Aizawa S, Tajika Y, Murakami T, Fu F H. Evaluation of ACL mid-substance cross-sectional area for reconstructed autograft selection. Knee Surg Sports Traumatol Arthrosc 2014; 22:207-213.

31. Werner, B., et al., "A Prospective evaluation of the anterior horn of the lateral meniscus as a landmark for tibial tunnel placement in anterior cruciate ligament (ACL reconstruction", The Knee 2016; 23: 478-481.

32. European Patent Application Publication No. EP2092900 A1, Re, Paul, "Device for orienting the tibial tunnel position during an ACL reconstruction", Aug. 26, 2009.

33. U.S. Pat. No. 5,562,664, Durlacher, et al., "Drill Guide with Target PCL-Oriented Marking Hook", Oct. 8, 1996.

34. U.S. Pat. No. 5,409,494, Morgan, C., "PCL Oriented Placement Tibial Guide", Apr. 25, 1995.

35. U.S. Pat. No. 5,269,786, Morgan, C., "PCL Oriented Placement Tibial Guide Method", Dec. 14, 1993.

36. U.S. Pat. No. 8,298,239 B2, Re, P., "Tibial Guide for ACL Repair Having Interchangeable and/or Rotatable Outrigger", Oct. 30, 2012.

37. U.S. Pat. No. 7,736,364 B2, Stone, K., "Method and Apparatus for Performing ACL Reconstruction", Jun. 15, 2010.

38. U.S. Pat. No. 6,254,605 B1, Howell, S., "Tibial Guide", Jul. 3, 2001.

39. U.S. Pat. No. 8,444,652 B2, Amis, et al., "Reconstruction of Anterior Cruciate Ligaments", May 21, 2013.

40. U.S. Patent Application Publication No. US2012/0059382 A1, Paulos, L., "Guide Systems and Methods for Ligament Reconstruction", Mar. 8, 2012.

41. Irarrazaval, S., et al., "Anterior cruciate ligament reconstruction", Journal of ISAKOS, 2016; 1:38-52. Doi: 10.1136/jlsakos-2015-000001.

42. American Academy of Orthopaedic Surgeons, *ACL Injury: Does it Require Surgery?*, OrthoInfo (September 2009), pp 1-11. https://orthoinfo.aaos.org/en/treatment/acl-injury-does-it-require-surgery.

43. Al-Amin M. Kassam, et al., *Anatomic Anterior Cruciate Ligament Reconstruction: The Use of the Anterior of the Lateral Meniscus as a Guide to Tibial Tunnel Placement*, Arthroscopy Techniques, Vol. 5, No. 4 (August), pp e809-e814 (2016).

44. Hiroki Shimodaira, et al., *Tibial Tunnel Positioning Technique Using Bony/Anatomical Landmarks in Anatomical Anterior Cruciate Ligament Reconstruction*, Vol. 6, No. 1 (February), Arthroscopy Techniques, pp e49-e55, (2017).

45. Jeremy M. Burnham, et al., *Anatomic Femoral and Tibial Tunnel Placement During Anterior Cruciate Ligament Reconstruction: Anteromedial Portal All-Inside and Outside-In Techniques,* 6 Arthroscropy Techniques, Vol. 6, No. 2 (April), e275-e282, (2017).

46. Thore Zantop, et al., *Tunnel Positioning of Anteromedial and Posterolateral Bundles in Anatomic Anterior Cruciate Ligament Reconstruction*, Am. J. Sports Med., Vol. 36, No. 1, pp 65-72. (2008).

47. http://www.smith-nephew.com/professional/products/all-products/acufex-director/.

48. http://www.boviemedical.com/cauteries.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

I claim:

1. An adjustable device for identifying a target location for a bone tunnel of a subject, said device comprising:
   a first arm comprising an anterior portion and a posterior portion opposite said anterior portion, wherein said posterior portion is configured to engage a reference structure;
   a targeting arm movably disposed on said first arm; wherein said targeting arm is configured to extend toward and engage across a region of an anatomic structure;
   a second arm comprising a superior portion and an inferior portion opposite said superior portion, wherein said superior portion of said second arm is in communication with said anterior portion of said first arm; and
   a measurement member slidably disposed on said second arm, wherein said measurement member and said second arm are configured to move relative to each other, and wherein said measurement member is configured to extend toward and engage a surface of the anatomic structure.

2. The device in claim 1, further comprising a targeting arm adjustment means disposed on said device, wherein said targeting arm adjustment means is configured to move said targeting arm relative to said first arm.

3. The device in claim 1, wherein said targeting arm is further configured to slide along said first arm.

4. The device in claim 1, wherein said targeting arm is configured to pivot about a fixed point on said first arm.

5. The device in claim 1, wherein said targeting arm is further configured to withdraw and lay flush against a surface of said first arm.

6. The device in claim 1, further comprising a guiding device disposed on said inferior portion of said second arm, wherein said guiding device is configured to receive a guide pin.

7. The device in claim 6, wherein said guiding device further comprises a guiding device adjustment means disposed on said guiding device, wherein said guiding device adjustment means is configured to adjust the angle of said guiding device relative to said second arm.

8. The device in claim 7, wherein said guiding device is further configured to rotate about a fixed point on said inferior portion of said second arm.

9. The device in claim 6, wherein said guide pin has a diameter of 3/32 of an inch.

10. The device in claim 1, wherein said second arm is convexly curved.

11. The device in claim 1, wherein said inferior portion of said second arm is further configured to engage a surface of the anatomic structure.

12. The device in claim 1, wherein the bone tunnel is a tibial bone tunnel.

13. The device in claim 1, wherein said first arm further comprises a plurality of graduated markings indicating units of length.

14. The device in claim 1, wherein said measurement member further comprises a plurality of graduated markings indicating units of length.

15. The device in claim 1, wherein said posterior portion of said first arm terminates in a curved hook, wherein said curved hook is configured to engage said reference structure.

16. The device in claim 1, wherein the reference structure is a posterior cruciate ligament.

17. The device in claim 1, wherein the reference structure is a posterior end of a tibial plateau.

18. The device in claim 1, wherein the region of the anatomic structure is a tibial plateau.

19. The device in claim 1, wherein said targeting arm is further configured to engage the anatomic structure at a target distance across the anatomic structure, said target distance corresponding to a predetermined percentage across the total distance across the anatomic structure, wherein said target distance is calculated in reference to said predetermined percentage and said total distance across the anatomic structure.

20. The device in claim 1, wherein said second arm further comprises an outer portion of said second arm, an inner portion of said second arm in communication with at least one surface of said outer portion, and a second arm adjusting means disposed on said second arm, wherein said second arm adjusting means is configured to alter a length of said second arm by slidably moving said inner portion of said second arm and said outer portion of said second arm relative to each other.

21. The device in claim 20, further comprising a means to separate said outer portion of said second arm and said inner portion of said second arm, wherein said outer portion of said second arm is offset from said inner portion of said second arm, and wherein said means to separate said outer portion of said second arm and said inner portion of said second arm is configured to allow said outer portion of said second arm and said inner portion of said second arm to move relative to each other.

22. The device in claim 20, wherein said outer portion of said second arm completely envelops said inner portion of said second arm.

23. The device in claim 20, wherein said outer portion of said second arm is disposed superiorly to said inner portion of said second arm.

24. The device in claim 20, wherein said outer portion of said second arm is disposed inferiorly to said inner portion of said second arm.

25. The device in claim 1, wherein said second arm further comprises a slot, wherein said slot is configured to accommodate said measurement member.

26. The device in claim 25, wherein said measurement member is further configured to slidably move within said slot.

27. The device in claim 25, wherein said second arm further comprises a measurement member adjustment means disposed on said second arm, wherein said measurement member adjustment means is configured to slidably adjust said measurement member within said slot.

28. The device in claim 25, wherein said measurement member further comprises a measurement member adjustment means disposed on said measurement member, wherein said measurement member adjustment means is configured to slidably adjust said measurement member within said slot.

29. The device in claim 1, wherein said adjustable device is composed of a material selected from the group consisting of surgical-grade stainless steel, titanium, aluminum, or plastic.

* * * * *